US012573490B2

(12) United States Patent
Lee

(10) Patent No.: US 12,573,490 B2
(45) Date of Patent: Mar. 10, 2026

(54) MEDICATION DELIVERY SIMULATION SYSTEM

(71) Applicant: Bigfoot Biomedical, Inc., Milpitas, CA (US)

(72) Inventor: Kevin S. Lee, Milpitas, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 729 days.

(21) Appl. No.: 17/996,039

(22) PCT Filed: Apr. 14, 2021

(86) PCT No.: PCT/US2021/070390
§ 371 (c)(1),
(2) Date: Oct. 12, 2022

(87) PCT Pub. No.: WO2021/212140
PCT Pub. Date: Oct. 21, 2021

(65) Prior Publication Data
US 2023/0187047 A1 Jun. 15, 2023

Related U.S. Application Data

(60) Provisional application No. 63/011,729, filed on Apr. 17, 2020.

(51) Int. Cl.
*G16H 20/17* (2018.01)
*A61M 5/142* (2006.01)
(52) U.S. Cl.
CPC ........ *G16H 20/17* (2018.01); *A61M 5/14244* (2013.01); *A61M 2005/14292* (2013.01)

(58) Field of Classification Search
None
See application file for complete search history.

(56) References Cited

U.S. PATENT DOCUMENTS 8,876,803 B2* 11/2014 Budiman ............... G16H 20/17
604/890.1
2014/0344280 A1* 11/2014 Wei ........................ G16H 40/60
707/740

(Continued)

FOREIGN PATENT DOCUMENTS

EP 2354990 A1 8/2011

OTHER PUBLICATIONS

International Search Report and Written Opinion for PCT Application No. PCT/US2021/070390, mailed on Jul. 8, 2021, 8 pages.

(Continued)

*Primary Examiner* — Manuel A Mendez
(74) *Attorney, Agent, or Firm* — Sterne, Kessler, Goldstein & Fox P.L.L.C.

(57) ABSTRACT

This document generally describes systems and methods for simulating a medication delivery system. Some embodiments can include a medication delivery simulation system that simulates an operation of a medication delivery system, such as delivery of a medication and detection of a response to the delivery. The simulation system can be used to simulate at least part of the operation of a medication delivery system and can check operations of one or more components in the medication delivery system, such as a pump, a sensor, a user device (e.g., a mobile device), and a server computing device.

21 Claims, 12 Drawing Sheets

(56)                 References Cited

U.S. PATENT DOCUMENTS

| | | |
|---|---|---|
| 2019/0192764 A1 | 6/2019 | Brewer et al. |
| 2019/0252079 A1* | 8/2019 | Constantin ............. G16H 70/20 |
| 2023/0154625 A1* | 5/2023 | Hayter ................... G16H 50/20 |
| | | 703/11 |
| 2023/0187047 A1* | 6/2023 | Lee ........................ G16H 50/20 |
| | | 604/504 |

OTHER PUBLICATIONS

Extended European Search Report for EP Application No. 21789149.
8, mailed on Mar. 21, 2024; 10 pages.

\* cited by examiner

400 ⟍

CGM Simulation System
100

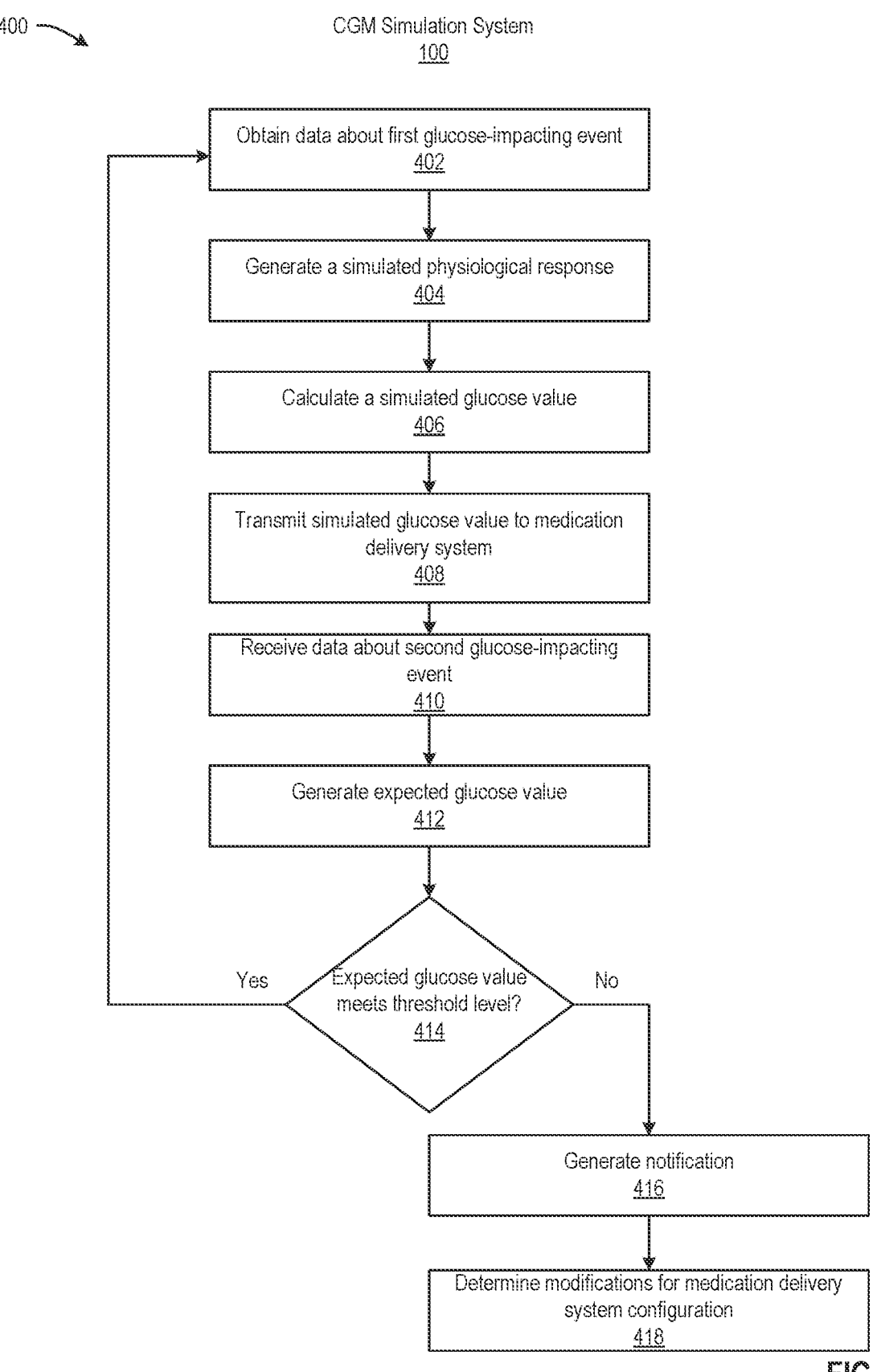

Obtain data about first glucose-impacting event
402

Generate a simulated physiological response
404

Calculate a simulated glucose value
406

Transmit simulated glucose value to medication delivery system
408

Receive data about second glucose-impacting event
410

Generate expected glucose value
412

Expected glucose value meets threshold level?
414

Yes          No

Generate notification
416

Determine modifications for medication delivery system configuration
418

FIG. 4

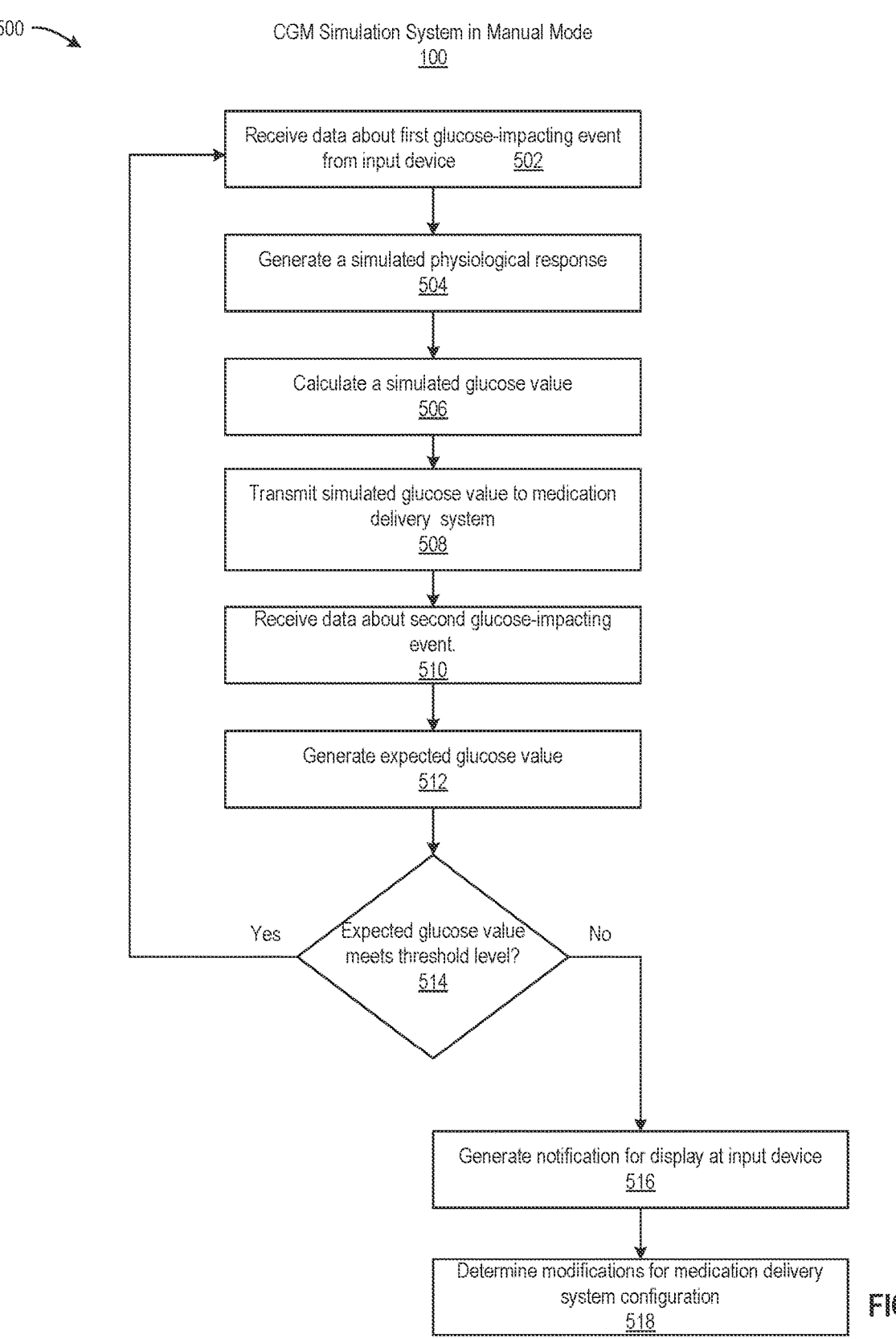

500

CGM Simulation System in Manual Mode
100

Receive data about first glucose-impacting event
from input device        502

Generate a simulated physiological response
504

Calculate a simulated glucose value
506

Transmit simulated glucose value to medication
delivery  system
508

Receive data about second glucose-impacting
event.
510

Generate expected glucose value
512

Expected glucose value
meets threshold level?
514

Yes        No

Generate notification for display at input device
516

Determine modifications for medication delivery
system configuration
518

FIG. 5

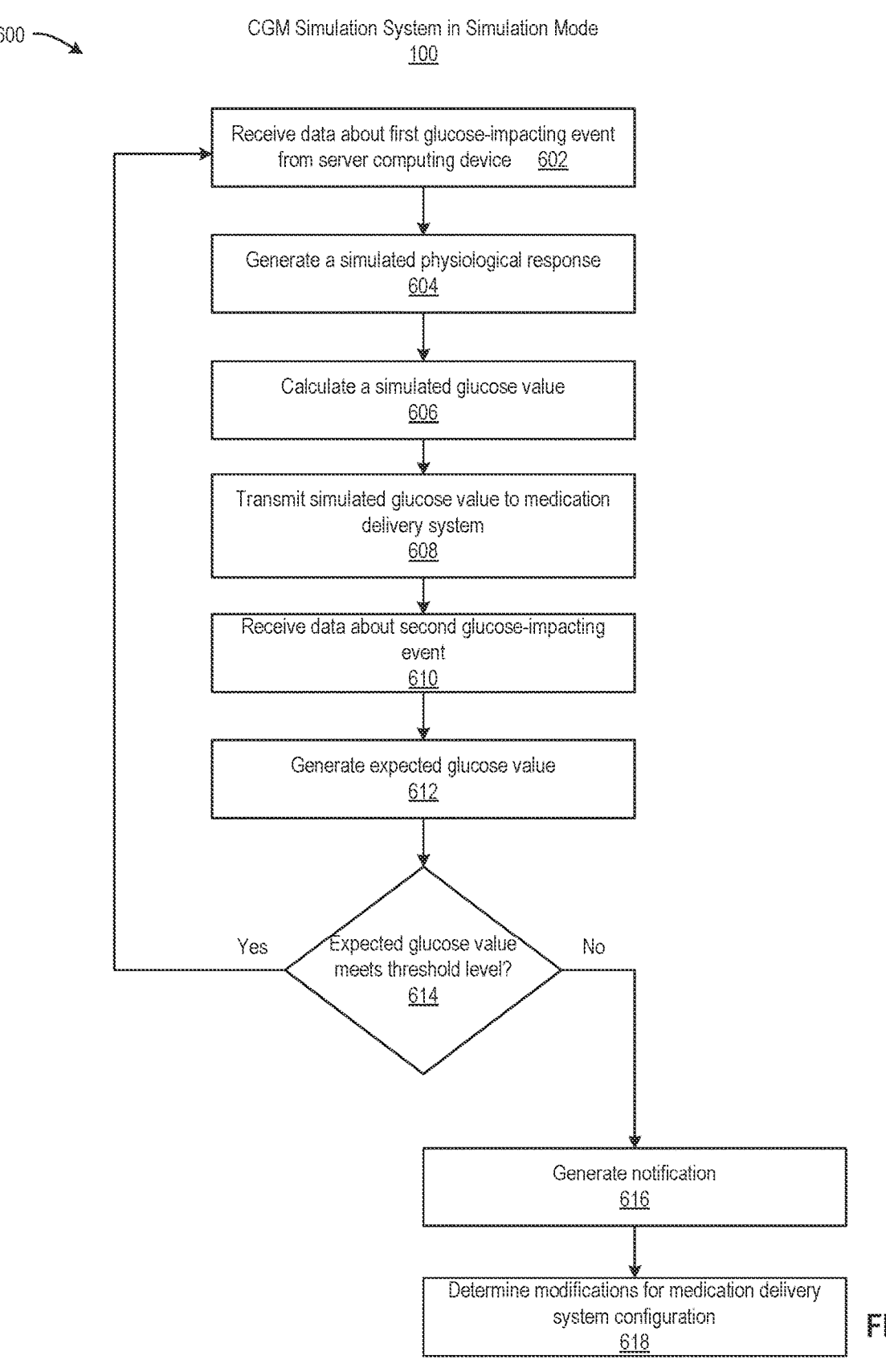

600

CGM Simulation System in Simulation Mode
100

Receive data about first glucose-impacting event
from server computing device    602

Generate a simulated physiological response
604

Calculate a simulated glucose value
606

Transmit simulated glucose value to medication
delivery system
608

Receive data about second glucose-impacting
event
610

Generate expected glucose value
612

Expected glucose value
meets threshold level?
614

Yes

No

Generate notification
616

Determine modifications for medication delivery
system configuration
618

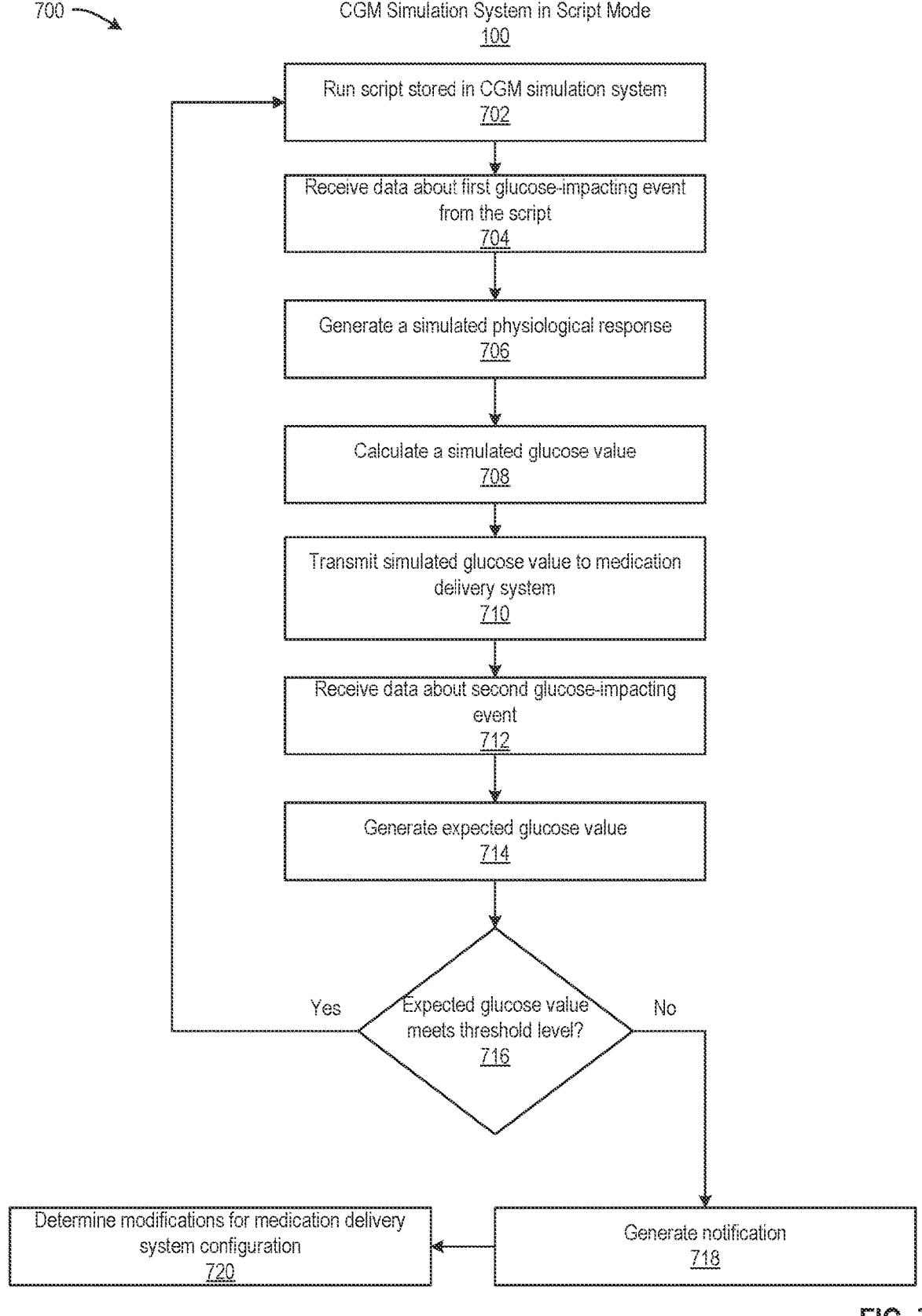

CGM Simulation System in Script Mode
100

Run script stored in CGM simulation system
702

Receive data about first glucose-impacting event
from the script
704

Generate a simulated physiological response
706

Calculate a simulated glucose value
708

Transmit simulated glucose value to medication
delivery system
710

Receive data about second glucose-impacting
event
712

Generate expected glucose value
714

Expected glucose value
meets threshold level?
716

Yes        No

Determine modifications for medication delivery
system configuration
720

Generate notification
718

CGM Simulation System
100

Input Device 102

Processor 106/ Conversion Module 110

Simulated Sensor 108

Obtain data about first glucose-impacting event
802

Generate a simulated physiological response
804

Calculate a simulated glucose value
806

Transmit simulated glucose value to medication delivery system
808

Go to FIG. 8B

CGM Simulation System 100

Processor 106 / Conversion
Module 110

Receive data about second
glucose-impacting event from
CGM system
810

Generate expected glucose value
812

Expected glucose value
meets threshold level?
814

Yes

No

Return to 802 in

Generate notification
816

Determine modifications for
medication delivery system
configuration
818

MEDICATION DELIVERY SIMULATION SYSTEM

CROSS-REFERENCE TO RELATED APPLICATIONS

This application is a 35 U.S.C. § 371 National Phase Entry Application from PCT Application No. PCT/US2021/070390, filed on Apr. 14, 2021, and designating the U.S., which claims priority to U.S. Provisional Application No. 63/011,729, filed on Apr. 17, 2020, entitled "MEDICATION DELIVERY SIMULATION SYSTEM," the disclosures of both of which are incorporated by reference herein in their entireties.

TECHNICAL FIELD

This document generally relates to systems and methods for simulating a medication delivery system.

BACKGROUND

Medication delivery systems can use pump devices to deliver fluids to a targeted individual. For example, a medical infusion pump device can be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels. The pump device can include, or communicate with, other components, such as a sensor device for detecting the patient's blood-glucose level, and a user device (e.g., a mobile phone or computer) for controlling the pump device.

The pump device can experience integration and/or communication issues with other components in a medication delivery system, thereby affecting accurate delivery of the fluids to the patient. Additionally, the pump device can experience power failures, which may result in delayed or missing delivery of the fluids to the target individual.

SUMMARY

This document generally describes systems and methods for simulating one or more components of a medication delivery system, such as a continuous glucose monitoring (CGM) device/system for a medication delivery system such as an insulin or glucagon delivery system. Some embodiments of a system includes a medication delivery simulation system that simulates an operation of a medication delivery system, such as delivery of a medication and detection of a response to the delivery. For example, the simulation system can be used to simulate at least part of the operation of a medication delivery system. The CGM simulation system can be used check operations of one or more components in the medication delivery system, such as a pump, a sensor, a user device (e.g., a mobile device), and a server computing device by simulating inputs that would normally be received from a CGM device. The CGM simulation system can further check an operation of the entire medication delivery system to determine whether the medication delivery system experiences communication and/or integration failures and/or whether information is accurately and timely transmitted to components of the medication delivery system. For example, in some embodiments, a simulation sensor at the CGM simulation system can communicate with a pump at the medication delivery system and transmit at least one glucose reading (e.g., a simulated glucose reading) to the pump, wherein the pump can perform its normal operations, such as calculating how much insulin to inject into a patient based on the received glucose reading. Here, the CGM simulation system can test whether the pump is operating correctly and is in proper communication with other components, such as a sensor, in the medication delivery system. In some implementations, the medical infusion device (pump) can be partially or completely disabled. For example, the medical infusion device can be configured to calculate medication delivery amounts but mechanical components can be disabled to prevent the pump from administering medication.

The systems and methods described herein can be used to test the medication delivery system at the manufacturing stage, or before the medication delivery system is given to a patient to verify that the components of the medication delivery system are functioning and/or communicating properly. Additionally or alternatively, the system and method described herein can be used to test the medication delivery system at any time by the patient or another user, such as a technician, to ensure the performance of the medication delivery system.

In some embodiments, the CGM simulation system described herein can include a computing device. A user can control the CGM simulation system from the computing device, which can be in communication with a server computing device, such as a cloud network, to receive physiological data. In some implementations, the server computing device can be a component of the medication delivery system and communicate with other components of the medication delivery system such as a medication delivery pump, a sensor (e.g., a blood glucose sensor or other physiological sensors), or a user device (e.g., a user's mobile device). The computing device in the CGM simulation system can be in further communication with the medication delivery system so as to test one or more components of the medication delivery system, such as the pump, the sensor, or the user device. In some embodiments, the CGM simulation system can receive a user input at the computing device that includes physiological data or other blood glucose impacting events (e.g., carb ingestion, exogenous insulin delivery, exercise, etc.) to then be used for testing the one or more components of the medication delivery system.

In some embodiments, the CGM simulation system can include a manual mode, a simulation mode, and a scripted mode. When the CGM simulation system is in the manual mode, the system described herein can receive physiological data or other blood glucose impacting event data from the user at the computing device and use that data in order to simulate/test the operation of the medication delivery system (including the communication among the components in the medication delivery system). When the CGM simulation system is in the simulation mode, the system described herein can receive, in real-time, physiological data or other blood glucose impacting event data (such as information on simulated or calculated medication delivery rates) relating to the medication delivery system from the server computing device in order to simulate and test the operation of the medication delivery system (including the communication among the components with the medication delivery system). When the CGM simulation system is in the scripted mode, the system described herein can obtain physiological data or other blood glucose impacting event data from a script that is preset to provide data representative of one or more predetermined blood glucose impacting events to the CGM simulation system, so that the CGM simulation system can simulate and test the medication delivery system based on the data. The script can be configured to run at a predetermined time (e.g., a particular time in a day, a particular day and time in a week, etc.). The script can include data representative of multiple blood glucose impacting events that can occur over a particular period of time (e.g., from 6 PM to 8 AM on the next day). The script can be stored in various locations. For example, the script can be stored in the CGM simulation system. In an alternative example, the script can be stored in the server computing device and transmitted to the CGM simulation system.

In some aspects of the invention, a method for simulating a glucose monitoring system, wherein the glucose monitoring system includes a medication delivery device configured to dispense medication, can include obtaining, at a simulation system, first data representative of a first glucose-impacting event. The method can further include generating, at the simulation system, second data based on the first data, the second data representative of a simulated physiological response to the first glucose-impacting event. The method can include calculating, at the simulation system, third data based on the second data, the third data representative of a simulated glucose value according to the simulated physiological response. The method can further include transmitting, using the simulation system, the third data to the glucose monitoring system, receiving, at the simulation system, fourth data from the glucose monitoring system, wherein the glucose monitoring system generates the fourth data representative of a second glucose-impacting event, generating, at the simulation system, fifth data based on the fourth data, the fifth data representative of an expected glucose value based on the second glucose-impacting event, determining, at the simulation system, whether the expected glucose value meets a threshold, and generating, at the simulation system, a notification based on the expected glucose value failing to meet the threshold. In some aspects of the invention, the simulation system can obtain the first data representative of the first glucose-impacting event at a first time, and receive the fourth data representative of the second glucose-impacting event at a second time later than the first time. The glucose monitoring system can additionally generate the fourth data based on the third data transmitted from the CGM simulation system. In some aspects of the invention, obtaining first data representative of a first glucose-impacting event can include receiving, at the simulation system, and from a server computer device, the first data representative of the first glucose-impacting event. In other aspects of the invention, obtaining first data representative of a first glucose-impacting event can include retrieving, at the simulation system, the first data representative of the first glucose-impacting event, wherein the first data is stored in the simulation system. In yet other aspects of the invention, obtaining first data representative of a first glucose-impacting event can include receiving, at the simulation system and from an input computing device, the first data representative of the first glucose-impacting event.

The first glucose-impacting event can include at least one of carb ingestion, exogenous insulin delivery, exercise, adjusted physiological parameter, system disconnection, or sensor fault. The first glucose-impacting event can also relate to a category of patients, wherein the category of patients can be based at least in part on an age, type of lifestyle, or type of diabetes. The second glucose-impacting event can include a dosage of the medication being calculated based on the simulated glucose value. The glucose monitoring system can further include a user computing device configured to communicate with the medication delivery device and a server computing device configured to communicate with the user computing device. The medication delivery device can include a medication injection pen.

In some aspects of the invention, a simulation system for a glucose monitoring system can include an input device configured to obtain first data representative of a first glucose-impacting event, a processor in communication with the input device, wherein the processor is configured to generate second data based on the first data, the second data representative of a simulated physiological response to the first glucose-impacting event, and a simulated sensor in communication with the processor, wherein the simulated sensor can be configured to generate third data based on the second data, the third data representative of a simulated glucose value according to the simulated physiological response, and transmit the third data to the glucose monitoring system. The processor can further be configured to receive, from the glucose monitoring system, fourth data representative of a second glucose-impacting event, generate fifth data based on the fourth data, the fifth data representative of an expected glucose value based on the second glucose-impacting event, determine whether the expected glucose value meets a threshold, and generate a notification based on the expected glucose value failing to meet the threshold. The fourth data can be generated, by the glucose monitoring system, based on the third data transmitted from the simulated sensor. The input device can be configured to obtain the first data representative of the first glucose-impacting event at a first time and the processor can be configured to receive the fourth data representative of the second glucose-impacting event at a second time later than the first time. The input device can also be configured to receive a user input of the first data representative of the first glucose-impacting event. In other aspects of the invention, the input device can be configured to receive the first data representative of the first glucose-impacting event from a server computing device. The simulation system can further include a storage device accessible by the processor, wherein the storage device can be configured to store at least one of a script and the first data representative of a plurality of glucose-impacting events including the first glucose-impacting event. The processor can configured to run the script to simulate the plurality of glucose-impacting events over a period of time, and generate the second data based on the plurality of glucose-impacting events.

One or more of the embodiments described herein can optionally provide some or all of the following advantages. First, the CGM simulation system can identify and resolve integration and/or communication issues between one or more components of the medication delivery system. In some implementations, the CGM simulation system can determine whether data has been accurately and reliably measured by, and transmitted among, components in the medication delivery system. For example, data that are critical to a patient's health, such as blood glucose level readings, calculated medication (e.g., insulin) dosages, medication dosages delivered to the patient, etc., need to be accurately detected by sensors (e.g., CGM sensors or other physiological sensors), and transmitted among the sensors, medication delivery pumps, user control devices (e.g., user mobile devices), and servers, so that an accurate dosage of medication is calculated and delivered to the patient at appropriate times. However, if there is an integration and/or communication failure and some or all of such data are not communicated between the components of the medication delivery system, the patient's health can be at risk (e.g., too high or low blood glucose level). Some implementations of the CGM simulation system described herein can be communicatively connected to a medication delivery system being tested by, for example, activating a simulated sensor in the CGM simulation system such that a communication is established between the simulated sensor and the pump of the medication delivery system. This communication can be used to test the operation of the pump, such as whether the pump is configured to connect and communicate with a sensor in order to receive and transmit data, and/or whether the pump can deliver an accurate dosage of medication to the patient. Further, the communication between the CGM simulation system and the medication delivery system can be used to test the operations of other components in the medication delivery system, such as a user device (e.g., a user mobile device that communicates with the pump), a server computer communicating with the pump and/or the user device, etc. For example, some implementations of the systems and methods disclosed herein can be advantageous to identify communication failures between components of the medication delivery system, including but not limited to the pump and a sensor, the pump and a mobile application, the mobile application and the server computing device, etc. The CGM simulation system can then determine appropriate notifications and/or responses to resolve and avoid these communication failures in real-time and also before a patient uses the medication delivery system.

Second, the CGM simulation system can use the simulated sensor to simulate a sensor (e.g., a blood glucose sensor) that is part of the medication delivery system and detect faults with the sensor. For example, the CGM simulation system can simulate the sensor of a CGM sensor that is accidentally removed from the patient's body or disconnected from another component of the medication delivery system. The CGM simulation system can determine when and what type of notification to generate upon such disconnection. If the CGM simulation system detects a loss of communication between the sensor (which can be simulated by the simulated sensor) and one or more components of the medication delivery system, the CGM simulation system can determine how to address the loss and provide an alert to the patient.

Third, the CGM simulation system can simulate and detect power loss failures and determine how to respond to such failures in the medication delivery system. For example, the CGM simulation system can simulate a power failure and an appropriate response, such as powering off a sensor (which can be simulated by the simulated sensor) and sending a notification to the patient that a battery needs to be replaced. As a result, this response can be easily and more readily implemented and integrated into the medication delivery system.

Fourth, the systems and methods described herein can focus on basal rate, insulin sensitivity factor, and carb ratio variables in order to determine physiological reactions to one or more events that are simulated by the CGM simulation system. Focusing on these variables can be advantageous because the CGM simulation system can simulate reactions and events that map onto a variety of patients in various states, including but not limited to infants, Type 1 Diabetes, sedentary individuals, and athletes. Over time, these variables can be algorithmically adjusted and learned by the CGM simulation system. In some embodiments, simulations can be run by the CGM simulation system that relate to different categories of patients. In other embodiments, simulations can be run by the CGM simulation system that relate to the physiological data of a particular patient.

The details of one or more embodiments are set forth in the accompanying drawings and the description below. Other features and advantages will be apparent from the description and drawings, and from the claims.

BRIEF DESCRIPTION OF DRAWINGS

FIG. 4 is a flowchart of an example process to simulate a medication delivery system.

FIG. 5 is a flowchart of an example process to simulate a medication delivery system in a manual mode.

FIG. 6 is a flowchart of an example process to simulate a medication delivery system in a simulation mode.

FIG. 7 is a flowchart of an example process to simulate a medication delivery system in a script mode.

DETAILED DESCRIPTION

Figure 1:
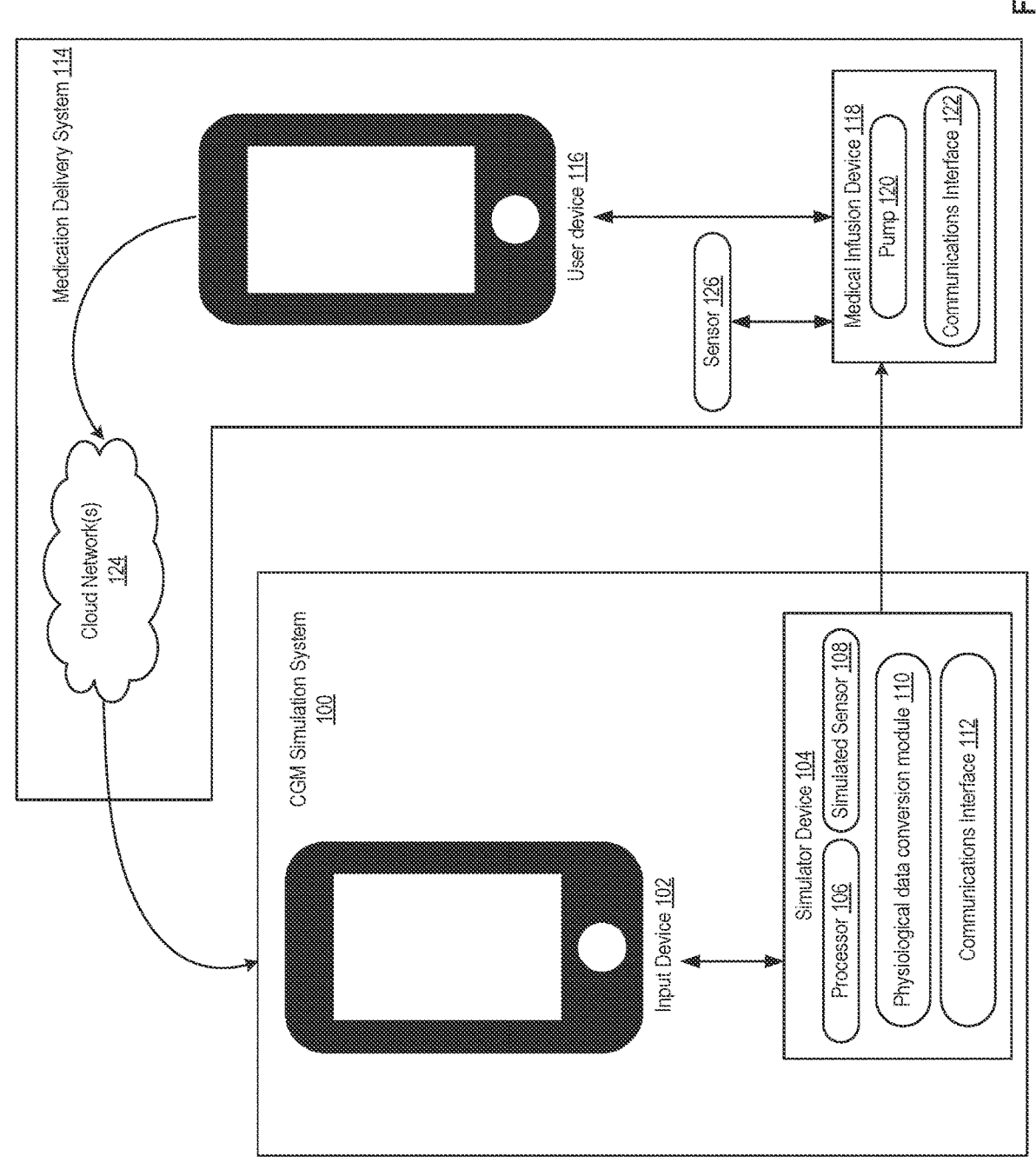
FIG. 1 is a block diagram of an example system for simulating a medication delivery system.

This document generally describes systems and methods for simulating one or more components of a medication delivery system, such as an insulin delivery system that includes a continuous glucose monitor (CGM). FIG. 1 is a block diagram of an example system 100 for simulating a medication delivery system 114. In this example, the system 100 is configured as a CGM simulation system for an insulin delivery system that is configured to interact with a CGM device. Thus, in this example, the system 100 can be also referred to as the CGM simulation system 100. The CGM simulation system 100 can communicate wirelessly (e.g., WIFI, BLUETOOTH) and/or wired with the medication delivery system 114. The CGM simulation system 100 can include an input device 102 and a simulator device 104. In some implementations, the simulator device 104 can be part of the input device 102. In other implementations, the device 104 can be in communication (e.g., wired and/or wireless) with the input device 102 and/or other components of the CGM simulation system 100. In the example depicted in FIG. 1, the input device 102 and the simulator device 104 are separate and communicate wirelessly with each other. The input device can be, for example, a laptop or desktop computer, a smartphone, a tablet device, or other known computing device.

Figure 2:
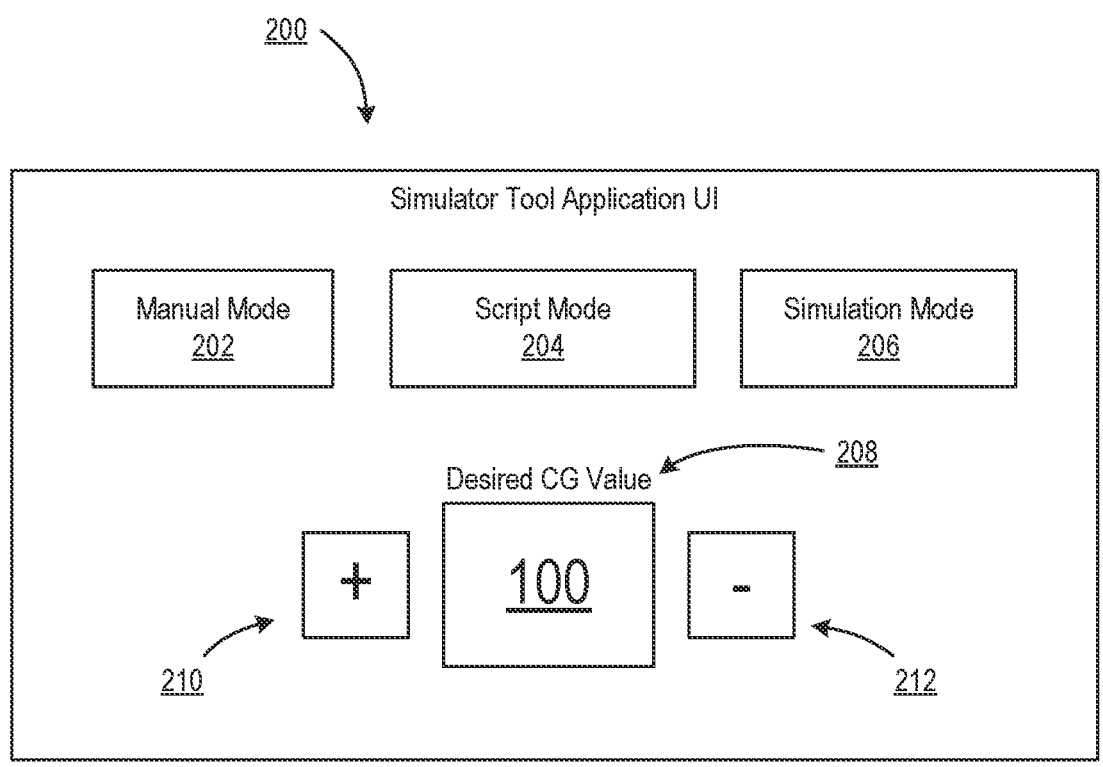
FIG. 2 schematically illustrates an example graphical user interface for the simulation system.

The input device 102 can receive and display information to a user. As illustrated in FIG. 2, the input device 102 can provide a user interface, such as a graphical user interface (GUI), that receives and displays information. For example, the input device 102 can include a display screen (e.g., LCD screen) and receive user input by touch, mouse, keyboard, and/or any other form of input device. In some implementations, such as when the CGM simulation system 100 is in a manual mode, the user (e.g., technician, tester) can use the input device 102 to input physiological data (e.g., simulated or actual physiological data) for the CGM simulation system 100 to communicate with and use in testing the medication delivery system 114 and its components. The CGM simulation system 100 can generate data that can impact a glucose value of a sensor based on the input received at the input device 102. In some implementations, in the manual mode, events that impact glucose values can be manually entered by the user. In other implementations, such as when the CGM simulation system 100 is used in a simulation mode, such glucose-impacting events can be obtained/retrieved from a cloud network 124 of the medication delivery system 114. In yet other implementations, such as when the CGM simulation system 100 is in a script mode, the glucose-impacting events can be run by a script that is locally stored in the CGM simulation system 100 or is retrieved from a remote database (e.g., the cloud network 124 or other database). Examples of the glucose-impacting events can include, but are not limited to, exogenous injection of medication (e.g., insulin), exercise, and unannounced carbs, basal and/or bolus delivery, and carb and other food ingestion.

Generally, the simulator device 104 can generate simulated physiological responses to event data inputs and convert such responses into raw values that can drive a sensor in the CGM simulation system 100 as well as in the real medication delivery system 114. The simulator device 104 can simulate conditions that can cause a simulated sensor (e.g., simulated sensor 108) to send data (e.g., CGM values) to and/or trigger faults in the real medication delivery system 114. In some implementations, the simulator device 104 can include at least a processor 106, a simulated sensor 108, a physiological data conversion module 110, and a communications interface 112. Data can be transmitted between the input device 102 and one or more components of the simulator device 104. In some implementations, one or more components of the simulator device 104 can be battery-operated. Alternatively or in addition, one or more components of the simulator device 104 can be powered by an external power source.

The simulated sensor 108 can simulate one or more sensors that are part of the medication delivery system 114. For example, the simulated sensor 108 can simulate a continuous glucose monitor or other blood glucose sensor. The simulated sensor 108 can be configured to calculate glucose values from received physiological data and communicate such values to components (e.g., a pump) of the medication delivery system 114. The simulated sensor 108 can be used to test and/or simulate operation and functionality of the medication delivery system 114 and one or more of its components (refer to FIGS. 9-10). In some implementations, an actual sensor can be used in place of the simulated sensor 108. For example, an actual continuous glucose monitor that is configured to detect blood glucose levels for a patient can be connected to a simulation device that simulates information that would be detected by the blood glucose monitor.

Still referring to FIG. 1, the simulator device 104 further can include the physiological data conversion module 110, which can be configured to generate responses, such as a physiological response, to the physiological data that may be manually inputted via the input device 102 (e.g., in the manual mode), transmitted from the cloud network 124 to the input device 102 (e.g., in the simulation mode), or locally stored and retrieved by the input device 102 (e.g., in the script mode). The responses generated can simulate or represent real responses that can be generated by the medication delivery system 114 when the medication delivery system 114 is in real-time operation. Additionally, in some implementations, the conversion module 110 can communicate with the processor 106 in order to generate simulated responses to the received physiological data. The processor 106 and/or the conversion module 110 can further be configured to convert generated simulated responses to raw values that can be communicated with the medication delivery system 114 in order to test the functioning of one or more components of the medication delivery system 114. In some implementations, the processor 106 can perform the functions of the conversion module 110. The communications interface 112 can be configured to allow communication (e.g., wired and/or wireless) between the simulator device 104 of the CGM simulation system 100 and the medication delivery system 114. Additionally, the communications interface 112 can facilitate communication between the CGM simulation system 100 and the cloud network 124.

In some implementations, the medication delivery system 114 can include the cloud network 124, a user device 116, a sensor 126, and a medical infusion device 118. In some implementations, the cloud network 124 may not be part of the medication delivery system 114 but rather is in communication (e.g., wirelessly) with the medication delivery system 114. In yet other implementations, the medication delivery system 114 can include additional components that are not depicted. The user device 116 can include a graphical user interface (GUI) to receive and display information to a user, such as a patient. The user device 116 can include a display screen (e.g., LCD screen) to display information in real-time to the patient. The user device 116 can display information such as current glucose levels/values of the patient, how much medication is being delivered to the patient, when the medication will be delivered, and other medication-related information. Additionally, the user device 116 can receive user input pertaining to glucose-impacting events, such as information about the patient's exercise and/or meal. In some implementations, the user device 116 can be a computer, smartphone, mobile device, and/or laptop.

Still referring to FIG. 1, the medical infusion device 118 can include a pump 120 and a communications interface 122. In some implementations, although not depicted, the medical infusion device 118 can include one or more sensors, such as a glucose monitoring sensor or other sensors that detect one or more physiological parameters of a patent. Such sensors can be of various types, such as a type being attached to a patient's body (e.g., a patch), a type being worn or carried by a patient (e.g., a wearable device), a type being implanted in a patient's body, etc. As depicted in FIG. 1, the medical delivery system 114 includes the sensor 126, which can communicate with the medical infusion device 118 by the communications interface 122. In some implementations, the sensor 126 can optionally communicate, via the communications interface 112, with the simulator device 104 of the CGM simulation system 100.

In the example depicted in FIG. 1, the medical infusion device 118 can communicate with the user device 116 to share information related to medication dosages. The pump 120, for example, can deliver a determined dosage of medication to the patient based on user-inputted information at the user device 116 indicating that the patient ate a carbohydrate-heavy meal. Further, as described herein, the medical infusion device 118 can communicate with the CGM simulation system 100 in order to test communication and integration of components of the medical infusion device 118, such as the pump 120, with the rest of the medication delivery system 114. In some implementations, the medical infusion device 118 can be partially or completely disabled. For example, the medical infusion device 118 can be configured to calculate medication delivery amounts but mechanical components can be disabled to prevent the pump from administering medication.

In some implementations, the medication delivery system 114 can communicate data to the cloud network 124. That data can then be communicated to the CGM simulation system 100. Based upon that data, the CGM simulation system 100 can generate simulated responses to the received data, generate glucose values, and communicate those back to the medication delivery system 114 in order to test the operation of the medication delivery system 114. This process can be considered a closed loop and/or the simulation mode and is advantageous to test the connection, communication, and integration of components of the medication delivery system 114 as well as to test responses of one or more components of the medication delivery system 114 (such as the medical infusion device 118 or user device 116) to changes in simulated detected blood glucose levels calculated and provided by the CGM simulation system 100. As a result of communication of data between the CGM simulation system 100 and the medication delivery system 114, the CGM simulation system 100 can receive more complex data and more accurately test the integration and functionality of the medication delivery system 114. In some implementations, the CGM simulation system 100 can further use this data to update components of the medication delivery system 114 (e.g., calibrate the pump 120, perform a software update, generate appropriate alerts and notifications for real-time use). The CGM simulation system 100 can further use this data to report any issues pertaining to communication, integration, and/or functionality of components of the medication delivery system 114 to the user (e.g., technician) at the input device 102.

In other implementations, the CGM simulation system 100 can receive data from the input device 102 and use that information to test the medication delivery system 114 without communicating with the cloud network 124. This implementation can be considered an open loop and/or the manual mode. Results or information associated with the testing of the medication delivery system 114 can be displayed at the input device 102, such that the user (e.g., technician) can ensure that the medication delivery system 114 is functioning properly and/or that its components are integrated and accurately communicating with each other. Based on the information displayed at the input device 102, the user can take appropriate steps to ensure that any communication, integration, and/or functionality issues with the medication delivery system 114 are resolved. The tester can resolve such issues before the medication delivery system 114 is given to a patient and used in real-time to dispense medication to the patient.

FIG. 2 is an example graphical user interface for the simulation system described herein. For example, the graphical user interface can include a simulator tool application UI 200. In some implementations, the UI 200 can be displayed at the input device 102 of the CGM simulation system 100. The UI 200 includes button options for a manual mode 202, a script mode 204, and a simulation mode 206. The UI 200 further includes buttons 210 and 212 for the user at the input device 102 to adjust a desired continuous glucose value 208. In other implementations, the user can input other values or data, such as a workout, meal, or delivered medication dosage.

As depicted, the CGM simulation system 100 can operate in 3 modes: manual, script, and simulation. The manual mode (button 202) can allow the user to manually adjust a glucose value or other data that is generated by the simulated sensor 108. When the CGM simulation system 100 is in manual mode, simulated physiological data or other blood glucose impacting event data can be received from the user (e.g., tester, technician) at the input device 102 and used to simulate/test operation and communication of the real medication delivery system 114 (refer to FIG. 5). Blood glucose impacting events that can be fed into the simulator include medication delivery amounts/rates calculated by, for example, the medical infusion device 118 of FIG. 1 such as bolus and basal insulin deliveries calculated by the medical infusion device 118. Blood glucose impacting events could also include scripted medication delivery amounts/rates. Blood glucose impacting events could also include simulated data on patient food consumption, patient activity (e.g., exercise), patient being asleep, and other activities related to a patient that could impact a patient's blood glucose levels. The blood glucose impacting events can also include time stamps indicating a time associated with a simulated blood glucose impacting event (e.g., time of bolus delivery or time of food consumption). As depicted, the user can use the buttons 210 and 212 in order to adjust the desired CG value 208 in the manual mode.

The script mode (button 204) allows the CGM simulation system 100 to receive a script that indicates the patient's (or a simulated patient's) typical behaviors. A series of events can be preprogrammed into the script, such that when the CGM simulation system 100 runs the script, specific events (e.g., one or more predetermined blood glucose impacting events) can be tested at specified times (refer to FIG. 7). As a result, the CGM simulation system 100 can simulate and test the real medication delivery system 114 based on the preset script. As discussed in FIG. 7, the script can be configured to run at particular, predetermined times and can include data representative of multiple glucose-impacting events that can occur over the particular period of time.

The simulation mode (button 206) can simulate physiological responses based on inputs that are received and/or observed at the user device 116 of the medication delivery system 114. The inputs can be based on a real patient's real-time conditions and use of the medication delivery system 114. The inputs can be communicated to the CGM simulation system 100 from the cloud network 124 (refer to FIG. 6). The CGM simulation system 100 can accordingly test and/or simulate operation and communication of the medication delivery system 114. For example, exogenous events that can impact a real patient's glucose levels can be received from the cloud network 124 and provided to the input device 102 in order to test/simulate communication and functionality of the real medication delivery system 114. Exemplary exogenous events include carbohydrate ingestion, exogenous insulin delivery, exercise, some form of disconnect, temporary or permanent adjustments to physiological parameters, and trigger sensor faults.

Figure 3:
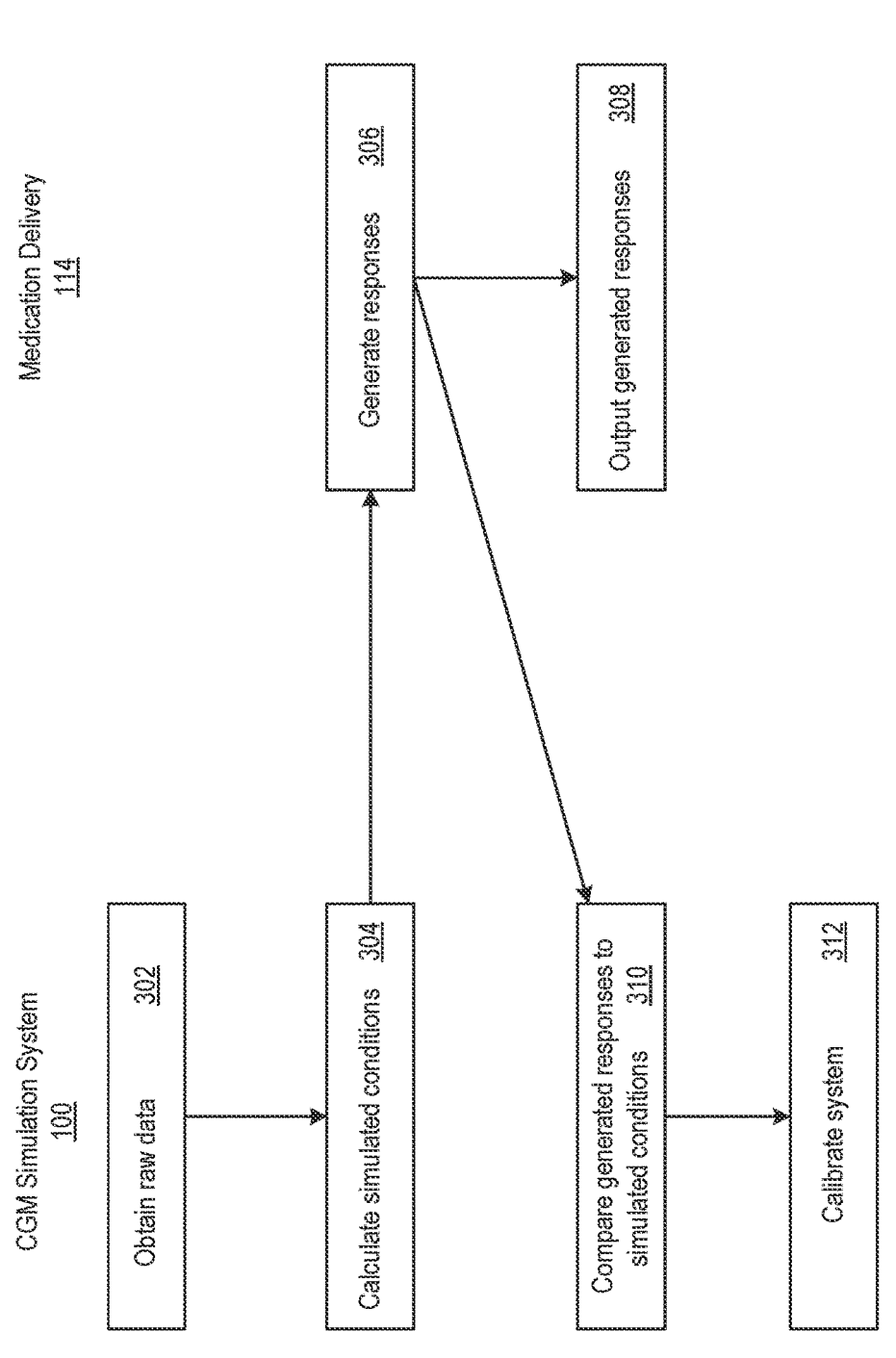
FIG. 3 is a flowchart of an example process to simulate a medication delivery system.

FIG. 3 is a flowchart of example process 300 to simulate the CGM monitoring and medication delivery system described herein (e.g., the system illustrated in FIG. 1). First, the CGM simulation system 100 can obtain raw data in step 302. The raw data can include information representative of events that may impact a glucose level of a patient. The CGM simulation system 100 can then calculate one or more simulated conditions based off the received data in step 304. The system 100 can further communicate the simulated conditions to the medication delivery system 114 in step 306. Then, the medication delivery system 114 can generate responses, such as determining how much medication (e.g., insulin) to deliver to the patient based on the simulated conditions (step 306). In the illustrated example of FIG. 1, the simulated sensor 108 at the CGM simulation system 100 can communicate at least one glucose reading to the pump 120 of the medication delivery system 114 such that the pump 120 can perform its normal operations and the CGM simulation system 100 can test those operations. The CGM simulation system 100 can test whether the pump 120 is operating correctly and/or in appropriate communication with other components, such as a sensor and user device 116, of the real medication delivery system 114.

Once responses are generated, the medication delivery system 114 can output the generated responses to the patient, for example, at the user device 116 (refer to FIG. 1) (step 308). In some implementations, the medication delivery system 114 can also communicate the generated responses back to the CGM simulation system 100. The CGM simulation system 100 can then compare the generated responses to the simulated conditions in step 310. Based on the comparison between the generated responses and the simulated conditions, the CGM simulation system 100 can determine whether the medication delivery system 114 is functioning properly and/or whether it is experiencing any communication and/or integration issues with components of the medication delivery system 114. Based on the determination made by the CGM simulation system 100, the system 100 can calibrate the medication delivery system 114 in step 312. Calibration can include resetting, restarting, and/or testing communication between components of the medication delivery system 114. In some implementations, the process 300 can repeat until the medication delivery system 114 experiences no more integration and/or communication issues. In yet other implementations, the process 300 can occur once and/or upon activation by the user at the input device 102 of the CGM simulation system 100 before the medication delivery system 114 is given to the patient to be used in real-time.

FIG. 4 is a flowchart of example process 400 to simulate the medication delivery system described herein. In the illustrated example of FIG. 1, the process 400 can be at least partially performed by the CGM simulation system 100, as described throughout this disclosure. First, the CGM simulation system 100 can obtain data about a first glucose-impacting event in step 402. In some implementations, the data can be inputted by a user at the input device 102 (e.g., manual mode, refer to FIG. 5). In other implementations, the data can be received from the cloud network 124 (e.g., simulation mode, refer to FIG. 6). In yet other implementations, the data can be transmitted directly from a mobile application at the user device 116 (refer to FIG. 1). In other implementations, the data can be obtained from a script (e.g., script mode, refer to FIG. 7). Exemplary first glucose-impacting events include, but are not limited to, an injection of insulin into a patient's body, a patient doing and/or logging exercise, and/or a patient eating and/or logging a meal.

Next, in step 404, the CGM simulation system 100 can generate a simulated physiological response based on the first glucose-impacting event. For example, the CGM simulation system 100 can simulate a glucose level response for a patient based on the patient eating and logging a carbohydrate heavy meal. By way of example, the CGM simulation system 100 can focus on a basal rate, insulin sensitivity factor, and/or carbohydrate ratio variable in order to determine simulated physiological responses to one or more events that are simulated by the CGM simulation system 100. These variables can be advantageous in order to simulate reactions and events that apply to a variety of patients in various states, such as infants, Type 1 Diabetes, sedentary individuals, elder people, and athletes. Over time, these variables can be algorithmically adjusted and learned over time by the CGM simulation system 100. As a result, the CGM simulation system 100 can more efficiently test/simulate the real medication delivery system 114 as it can be used and applied to a variety of patients.

Referring back to FIG. 4, the CGM simulation system 100 can calculate a simulated glucose value in step 406. Similarly to the medication delivery system 114, the CGM simulation system 100 can generate a simulated glucose value based on the simulated glucose level response that is generated in step 404 (refer to FIG. 1). In step 408, the CGM simulation system 100 can transmit the simulated glucose value to the medication delivery system 114. For example, the CGM simulation system 100 can transmit the simulated glucose value to the pump 120 of the medical infusion device 118 (refer to FIG. 1). The pump 120 in the real medication delivery system 114 can operate based on the received simulated glucose value. This step can be advantageous to test certain features of the real medication delivery system 114 and to determine whether the medication delivery system 114 is functioning properly. In some implementations, the pump 120 can be configured to calculate an appropriate insulin dosage to provide to a patient based on the received simulated glucose value. In other implementations, the pump 120 can further dispense that calculated insulin dosage to the patient.

Next, in step 410, the CGM simulation system 100 can receive data about a second glucose-impacting event. In some implementations, the data can be generated by the medication delivery system 114 based on the previous step, step 408. For example, the medication delivery system 114 can deliver a dosage of insulin to a patient based on the received simulated glucose value from the CGM simulation system 100. The delivery of insulin to the patient can be the second glucose-impacting event, which is then transmitted to the CGM simulation system 100.

In step 412, the CGM simulation system can generate an expected glucose value. The expected glucose value can be based off the second glucose-impacting event. For example, the CGM simulation system 100 can independently calculate what glucose value to dispense to a patient by the pump 120, based at least in part on the insulin dosage (e.g., second glucose-impacting event) previously delivered to the patient. The CGM simulation system 100 can then determine whether the expected glucose value meets a predetermined threshold level in step 414. In this step, the CGM simulation system 100 can be configured to determine whether the pump 120, for example, is in proper communication and/or integration with the rest of the real medication delivery system 114. More generally, in step 414, the CGM simulation system 100 can determine whether the entire medication delivery system 114 is working properly. The medication delivery system 114 requires data communication and integration between all components. When a communication signal goes out, data cannot be transmitted to other components of the medication delivery system 114. Consequently, some components cannot function properly, determine an appropriate glucose level, and/or dispense an appropriate insulin dosage. The CGM simulation system 100 can consider whether the components of the medication delivery system 114 are working correctly based on the expected glucose value falling within an acceptable range.

If the CGM simulation system 100 determines that the expected glucose value meets the predetermined threshold level in step 414, then the simulation system 100 can restart the process 400, either subsequently or at a later scheduled time. The steps previously described can be repeated. In some implementations, the steps can be repeated until an issue is identified by the CGM simulation system 100. For example, the simulation system 100 can repeat the process 400 until communication fails between the simulated sensor 108 of the CGM simulation system 100 and the pump 120 of the medication delivery system 114. In yet other implementations, the steps may not repeat once it is determined that the expected glucose value meets the predetermined threshold level. This can indicate that there are no communication or integration issues between components of the real medication delivery system 114 and that the medication delivery system 114 is ready to be used by a patient.

If the CGM simulation system 100 determines that the expected glucose value does not meet the predetermined threshold level in step 414, then the simulation system 100 can generate a notification in step 416 and can determine one or more modifications for the medication delivery system 114's configuration in step 418. Additionally, the simulation system 100 can set and/or update physiological parameters that are used by the simulator device 104 for later operations of the simulation system 100. The notification is generated as an alert, which can be transmitted to the user (e.g., technician) at the input device 102 of the CGM simulation system 100. The alert can include a listing and/or description of any identified issues with the medication delivery system 114. The user can then take appropriate action to respond to and/or correct the identified issue(s), such as updating one or more physiology parameters. Once the user makes such updates, additional testing/simulating can occur to test the modified configuration(s). In some implementations, the simulation system 100 can generate and transmit a notification/alert to the user device 116 and/or other components of the real medication delivery system 114. The notification/alert can then be captured and timestamped, then transmitted to the CGM simulation system 100. The CGM simulation system 100 can optionally compare captures of notifications/alerts generated, transmitted, and displayed at different components of the real medication delivery system 114 in order to determine whether there are communication issues and/or whether the user device 116 is receiving appropriate notifications.

Data critical to a patient's health, such as blood glucose level readings, calculated medication dosages, and medication dosages delivered to the patient need to be accurately detected by sensors (e.g., CGM sensors that are integrated into the medication delivery system 114 and/or other physiological sensors) and transmitted among the sensors, medication delivery pumps (e.g., the pump 120), user mobile devices (e.g., the user device 116), and server computing devices (e.g., the cloud network 124). Accurate transmission of critical data ensures that an accurate dosage of medication is calculated and delivered to the patient at appropriate times. However, if there is an integration and/or communication issue and some or all of such data are not communicated between the components of the real medication delivery system 114, then the patient's health can be at risk.

In some implementations, the issue can be a communication problem between the simulated sensor 108 of the CGM simulation system 100 and the pump 120 of the medication delivery system 114. For example, the simulated sensor 108 can speak two protocols: one can be NFC radio connection for activation of the simulated sensor 108 and the other can be BLUETOOTH for communication between the simulated sensor 108 and the pump 120.

Once NFC radio connection is established, the CGM simulation system 100 can verify that putting the simulated sensor 108 and the pump 120 a certain distance from each other results in BLUETOOTH communication of simulated glucose values to the pump 120 at the real medication delivery system 114. Where the NFC radio connection does not activate the simulated sensor 108, a communication issue exists between the simulated sensor 108 and the pump 120. Because of the communication issue, simulated glucose values cannot be transmitted to the pump 120 at the real medication delivery system 114.

In some implementations, the NFC radio connection can be used to activate the simulated sensor 108 in relation to other components of the real medication delivery system 114, including but not limited to the user device 116. Communication failures can indicate that data is not being received and/or transmitted between the pump 120 and the simulated sensor 108, the pump 120 and a mobile application at the user device 116, or the user device 116 and the cloud network 124. In other implementations, focusing on the communication between the simulated sensor 108 and the pump 120 can be advantageous to test the entire medication delivery system 114 because if communication goes down between these components, then all of the components of the medication delivery system 114 cannot accurately perform their functions or communicate accurate data to each other. Thus, communication can be tested amongst different components of the real medication delivery system 114 to ensure that the entire medication delivery system 114 functions properly when used by a real patient.

In some implementations, communication failures can be simulated at 2 points in the CGM simulation system 100. For example, communication failure can occur between the input device 102 and the cloud network 124 and/or between the simulator device 104 and the input device 102. Communication failure at both these points can be real-world functional equivalents of a disconnected infusion site with the medication delivery system 114 (e.g., refer to FIG. 9). Where such communication failure occurs, physiological responses continue to be generated by the medication delivery system 114 and will not be impacted by any events, such as the disconnected infusion site, reported by the medical infusion device 118. Therefore, during a simulated communication failure in the CGM simulation system 100, the processor 106 of the simulator device 104 can continue generating sensor glucose values based on previously recorded inputs/data and the CGM simulation system 100 can determine an appropriate response/alert/notification to handle and/or resolve the simulated communication issue.

Figure 9:
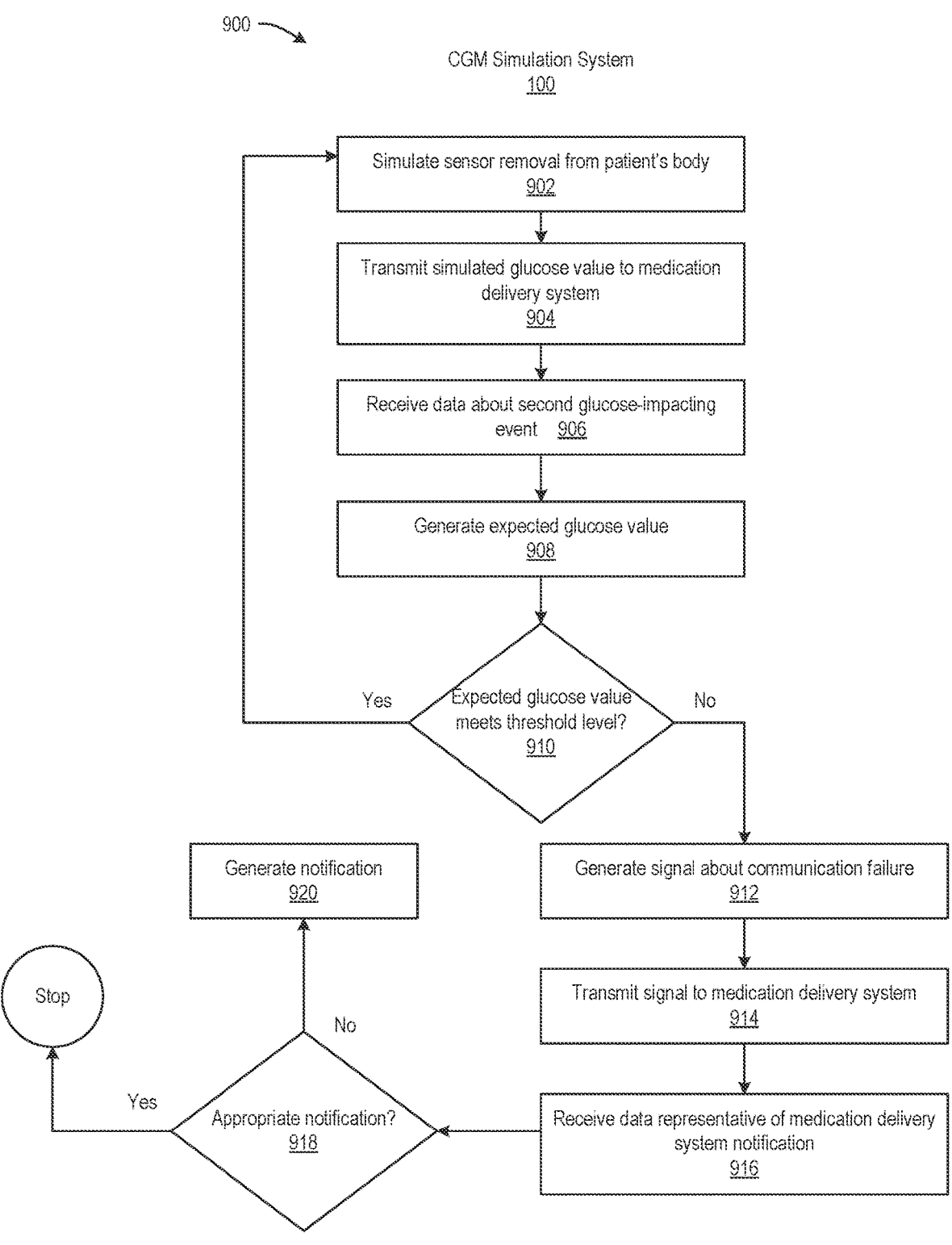
FIG. 9 is a flowchart of an example process to simulate a communication failure at a medication delivery system.
Figure 10:
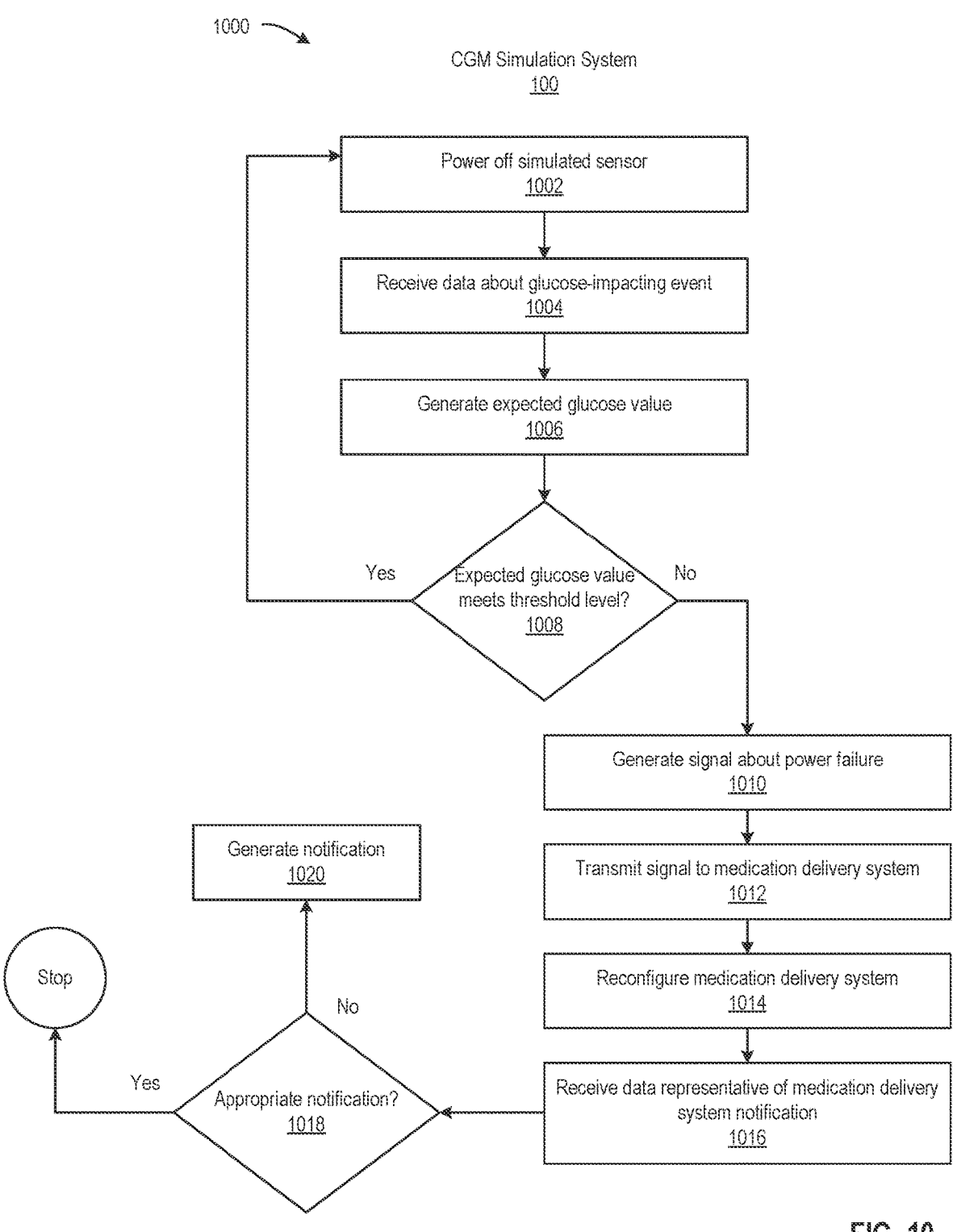
FIG. 10 is a flowchart of an example process to simulate a power loss failure at a medication delivery system.

In yet other implementations, since the simulator device 104 can be battery-operated, a power loss at the simulator device 104 can simulate a real-world functional equivalent of a sensor being ripped out of a patient, a sensor losing its power supply, and/or a sensor being placed out of range with other components of the real medication delivery system 114 (e.g., refer to FIGS. 9-10). Therefore, the CGM simulation system 100 can determine an appropriate response/alert/notification to handle and/or resolve the simulated power loss.

Referring back to FIG. 4, upon determining one or more modifications to the medication delivery system 114's configuration in step 418, the CGM simulation system 100 can repeat the process 400. Repeating the process 400 can be advantageous in order to determine whether the determined modifications in fact can fix the identified issue(s). The medication delivery system 114 then can optionally implement one or more of the modifications to the system 114's configuration. In some implementations, the process 400 can repeat within a certain period of time. For example, the user can run a script at the CGM simulation system 100, wherein the script can run the process 400 at particular times (e.g., once in a simulated morning, once in a simulated afternoon, and once in a simulated night. Refer to FIG. 7). In some implementations, the process 400 can be run at a particular time and/or by a command of the user at the input device 102. In yet other implementations, some steps of the process 400 can be performed at particular predetermined times. For example, some steps, such as steps 402-406 can be performed at a first time. Then, a certain amount of time can pass before other steps, such as steps 408-418 are performed. Staggering times at which particular steps in the process 400 are performed can be advantageous to test and simulate different situations in which the real medication delivery system 114 is used by a patient. For example, staggering times at which particular steps are performed can simulate patient inactivity, delays in communication of components of the medication delivery system 114, and/or temporary disconnection or integration issues between components of the medication delivery system 114.

FIG. 5 is a flowchart of example process 500 to simulate the medication delivery system in manual mode. For example, in manual mode, a glucose value inputted at the input device 102 can be used by the CGM simulation system 100 until a new value is inputted at the input device 102 (refer to FIG. 1). Previous inputted values and/or glucose impacting events may not influence a value simulated at the simulated sensor 108. The purpose of the process 500 is to push exogenous events that can have an impact on how components of the real medication delivery system 114 should respond. In manual mode, the medical infusion device 118 and the user device 116 may still react to values simulated in the process 500, however the CGM simulation system 100 may not receive notifications from the medication delivery system 114 about how one or more of the components of the system 114 respond to the simulated values (refer to FIG. 1).

As depicted, the process 500 can occur at the CGM simulation system 100, as described throughout this disclosure. The process 500 performs similarly to the process 400 depicted in FIG. 4 and described throughout this disclosure. First, in step 502, the CGM simulation system 100 can receive data about a first glucose-impacting event from the input device 102 (refer to FIG. 1). A user, such as a tester and/or technician can manually input physiological data into an application/graphical user interface that is displayed at the input device 102. Thus, the user can generate an exogenous event. Exemplary data can include a current glucose level for a patient and/or a category or grouping of patients.

The CGM simulation system 100 can generate a simulated physiological response in step 504 and based on the inputted physiological data. Step 504 can be performed at the processor 106 and/or the physiological data conversion module 110. The CGM simulation system 100 can calculate a simulated glucose value based on the simulated physiological response in step 506. Step 506 can be performed by the simulated sensor 108. Then, in step 508, the CGM simulation system 100 can transmit the simulated glucose value to the real medication delivery system 114, particularly to the pump 120. The CGM simulation system 100 can receive data about a second glucose-impacting event in step 510. This step can test, for example, whether the pump 120 accurately received the simulated glucose value from the simulated sensor 108 and whether the pump 120 used that value to measure how much insulin to deliver to a patient. Based on the data about the second glucose-impacting event, the CGM simulation system 100 can generate an expected glucose value in step 512. Then, in step 514, the CGM simulation system 100 can determine whether the expected glucose value meets a predetermined threshold level. If it does, then the CGM simulation system 100 can repeat the process 500, as this would indicate that communication is successful between components of the CGM simulation system 100 and the real medication delivery system 114. If it does not, then the CGM simulation system 100 can generate a notification for display at the input device 102 in step 516. In some implementations, the notification can be displayed at the user device 116 of the real medication delivery system 114. The notification can indicate what type of issue was identified, such as a communication failure between the simulated sensor 108 and the pump 120. Based on the generated notification, the CGM simulation system 100 can determine one or more modifications for the medication delivery system 114's configuration in step 518 in order to resolve the identified issue. Additionally, although not depicted, the simulation system 100 can repeat the process 500 after step 518 in order to test and/or determine whether the determined modifications to the medication delivery system 114's configuration are successful in resolving the identified issue. In some implementations, the real medication delivery system 114 can determine whether to implement the modifications generated by the simulation system 100 in step 518.

In some implementations in manual mode, the medical infusion device 118 can transmit values such as the expected glucose value to the user device 116 for display. This can simulate real integration and communication between components of the real medication delivery system 114. For example, in real-time, a patient can receive an update at the user device 116 that an amount of insulin will be or was delivered to the patient by the medical infusion device 118. Additionally, in some implementations, the notifications generated by the simulation system 100 in step 516 can be displayed at the user device 116.

FIG. 6 is a flowchart of example process 600 to simulate the medication delivery system in simulation mode. As depicted, the process 600 can occur at the CGM simulation system 100, as described throughout. The process 600 performs similarly to the process 400 depicted in FIG. 4 and described herein. The purpose of the process 600 is to retrieve glucose events that can impact how components of the real medication delivery system 114 should respond. In simulation mode, the CGM simulation system 100 can receive data about a first glucose-impacting event from a server computing device (e.g., the cloud network 124. Refer to FIG. 1) in step 602. In some implementations, a user at the input device 102 of the CGM simulation system 100 can request data from the server computing device. In other implementations, the CGM simulation system 100 can automatically receive data from the server computing device. For example, insulin delivery events can be generated at the pump 120 of the medical infusion device 118, transmitted to the user device 116, and then stored in the cloud network 124. The CGM simulation system 100 can automatically receive data about how much insulin was delivered and/or what time the insulin was delivered from the cloud network 124. In yet other implementations, a component of the simulator device 104, such as the processor 106, can request data and that request can be sent to the server computing device.

The server computing device can be the cloud network 124 as depicted in FIG. 1. The cloud network 124 can store glucose levels associated with each patient that uses real medication delivery systems. In other implementations, the cloud network 124 can store fake data, not associated with real patients, to test different possible scenarios, patients, and/or groups of patients. In some implementations, data stored in the cloud network 124 can be associated with different categories of patients. The categories of people can be based on, for example, age, lifestyle, and athleticism.

Still referring to step 602, in some implementations, the CGM simulation system 100 can receive data once every 5 minutes. This can be preferred because the simulated sensor 108 transmits glucose data every minute and the pump 120 in the medical infusion device 118 uses every 5th glucose data point. A 5 minute granularity can be sufficient to simulate necessary glucose changes, rather than sending event updates at 1 minute intervals. Because of background processing restrictions, an optimal way to get necessary processing time on targeted platforms (e.g., iOS and ANDROID) is to have the processor 106 of the simulator device 104 periodically wake the input device 102 with data requests. Once the input device 102 receives a data request, it can act as a proxy and request that data from the cloud network 124 in the simulation mode.

Next, in step 604, the CGM simulation system 100 can generate a simulated physiological response. Then the simulation system 100 can calculate a simulated glucose value in step 606 based on the simulated physiological response. The simulation system 100 can transmit the simulated glucose value to the medication delivery system 114 in step 608. In step 610, the simulation system 100 can receive data about a second glucose-impacting event. The CGM simulation system 100 can generate an expected glucose value based on the data about the second glucose-impacting event in step 612. The CGM simulation system 100 can determine whether the expected glucose value meets a predetermined threshold level in step 614. If it does, then the simulation system 100 can repeat the process 600. In other implementations, the process 600 can stop at step 614, which can indicate that simulation is complete. If the CGM simulation system 100 determines that the expected glucose value does not meet the predetermined threshold level in step 614, then the simulation system 100 can generate a notification at step 616 and determine one or more modifications for the medication delivery system 114's configuration in step 618. In some implementations in simulation mode, the medical infusion device 118 can transmit values such as the expected glucose value to the user device 116 for display. This can simulate real integration and communication between components of the real medication delivery system 114. For example, while in simulation mode, a virtual patient can receive an update at the user device 116 that an amount of insulin will be or was delivered to the virtual patient by the medical infusion device 118.

FIG. 7 is a flowchart of example process 700 to simulate the medication delivery system in script mode. As depicted, the process 700 can occur at the CGM simulation system 100, as described throughout this disclosure. The process 700 performs similarly to the process 400 depicted in FIG. 4 and described throughout this disclosure. First, the CGM simulation system 100 can run a script in step 702. The script can be stored (e.g., in memory) at the CGM simulation system 100. In some implementations, the script can be stored in the cloud network 124 and transmitted to the CGM simulation system 100. The CGM simulation system 100 can store a plurality of different scripts, wherein each script encompasses a different scenario, conditions, and/or characteristics associated with a patient or group of patients. For example, a script can simulate events associated with a particular patient at particular times during a 24-hour day. The script can include an event that takes place in the morning indicative of a first meal. The script can also include an event during the day that indicates an exercise activity. The script can further include an events in the evening indicative of a second meal and going to sleep asleep. The scripts can be based off of real data associated with patients that use the real medication delivery systems. In other implementations, the scripts can be based off fake data for the purpose of testing real medication delivery systems before they are used by real patients.

Referring back to FIG. 7, the CGM simulation system 100 can receive data about a first glucose-impacting event from the script in step 704. As mentioned, the first glucose-impacting event can be a scheduled first meal of the day. In some implementations, the simulation system 100 can receive data about a first glucose-impacting event from the input device 102 (refer to FIG. 1). Unlike the simulation system 100 in manual mode (refer to FIG. 5), the data received from the input device 102 can be used in a continuous loop throughout the process 700. Additionally and/or optionally, the received data can be a pre-executed simulation (e.g., based on a script) or the data can be one or more random values (e.g., based on input received at the input device 102). Like the simulation system 100 in manual mode (refer to FIG. 5), one or more previous values and/or glucose-impacting events may not influence values generated and simulated at the simulation system 100. Next, in step 706, the CGM simulation system 100 can generate a simulated physiological response. The simulation system can further be configured to calculate a simulated glucose value based on the simulated physiological response in step 708. Next, the simulation system 100 can transmit the simulated glucose value to the medication delivery system 114 in step 710. The CGM simulation system 100 can then receive data about a second glucose-impacting event in step 712 and generate an expected glucose value based off the second glucose-impacting event in step 714. Then, the CGM simulation system 100 can determine whether the expected glucose value meets a predetermined threshold in step 716. If it does, then the simulation system 100 can repeat the process 700. In some implementations, the process can stop at step 716. If the simulation system 100 determines that the expected glucose value does not meet the predetermined threshold level in step 716, then the simulation system 100 can generate a notification in step 718 and appropriately determine one or more modifications for the medication delivery system 114's configuration in step 720.

Figure 8A:
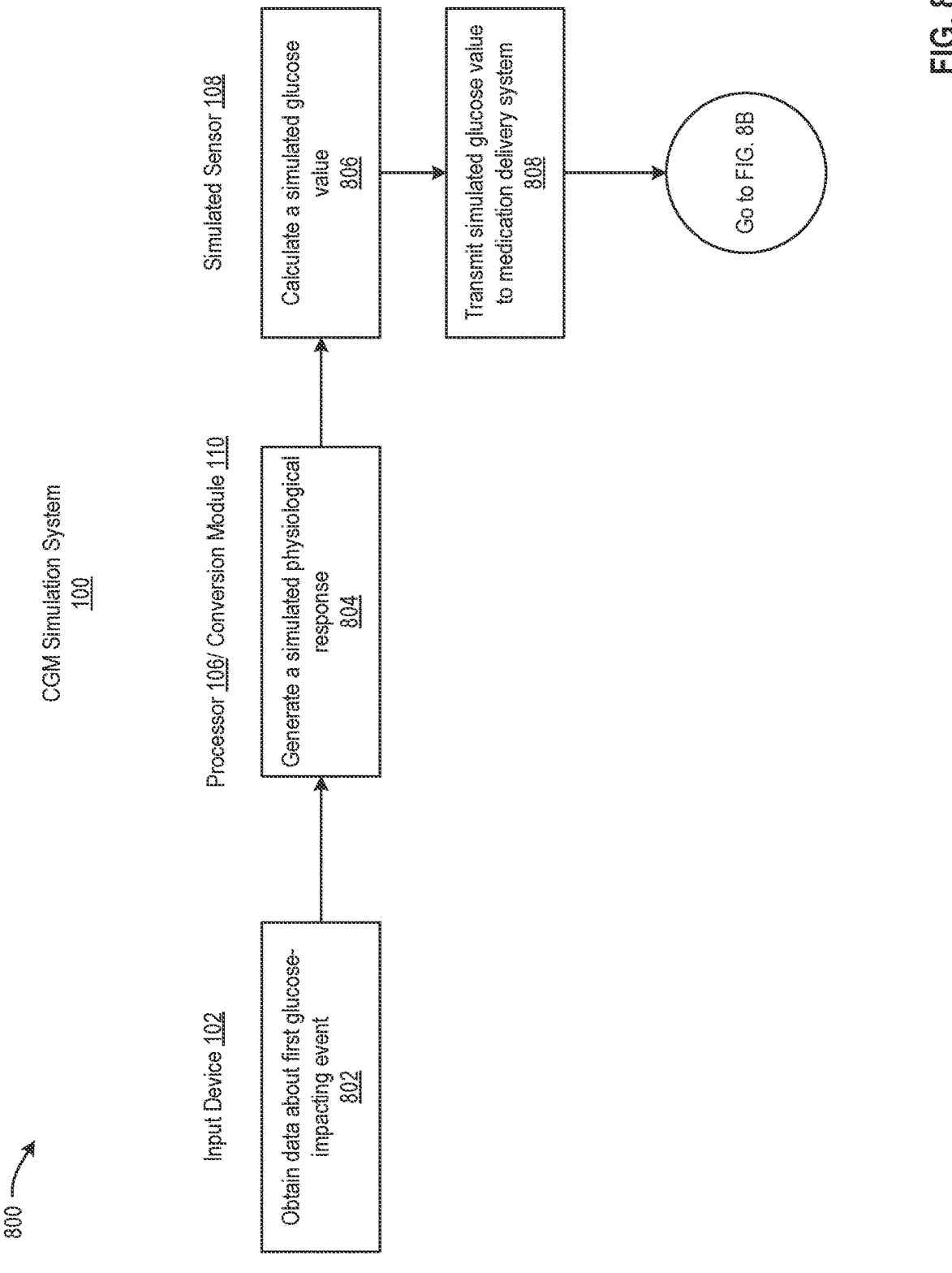
FIGS. 8A-B depict flowcharts of an example system for simulating a medication delivery system.
Figures 8A, 8B:
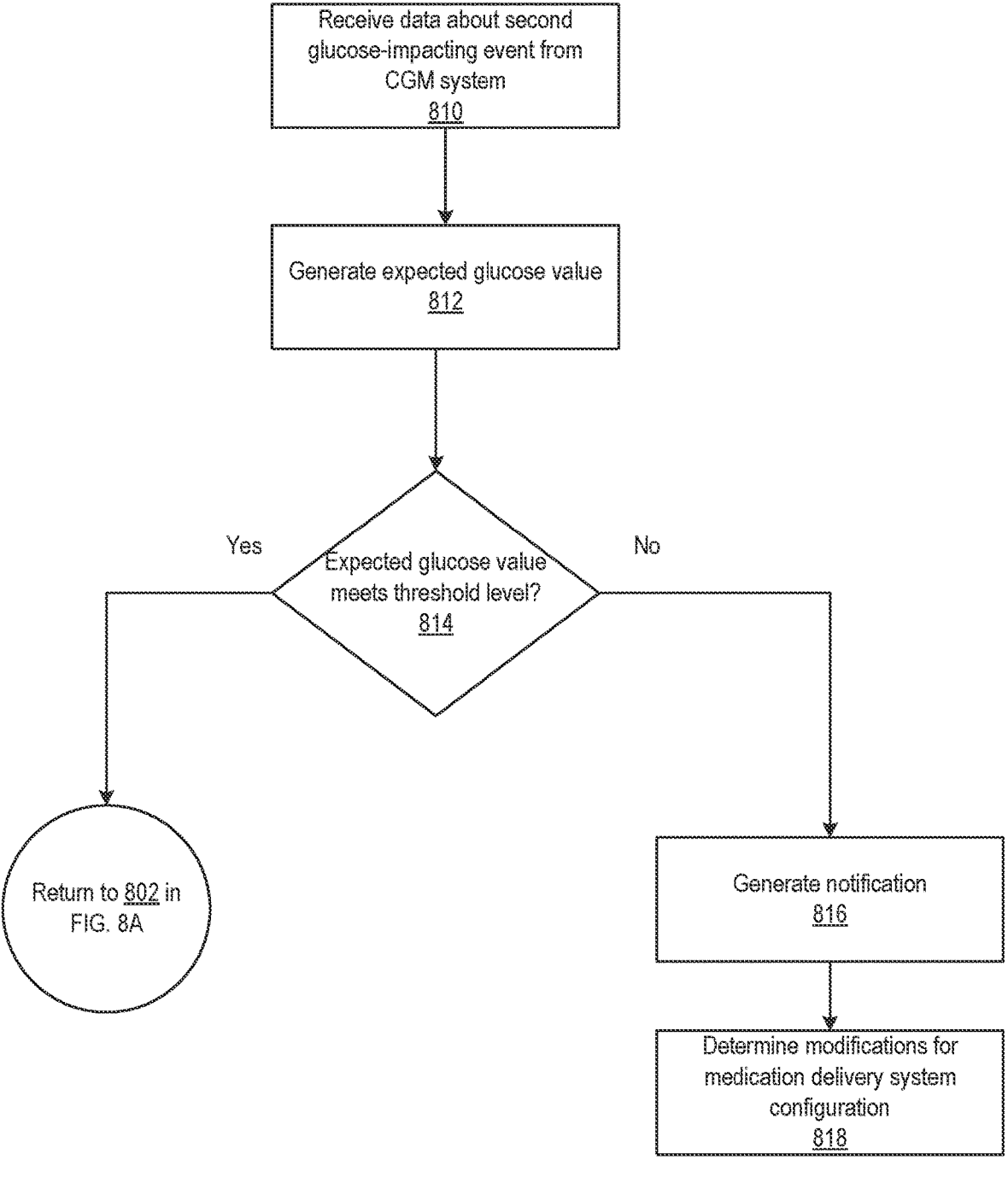

FIGS. 8A-B depict flowcharts of an example medication delivery system described herein. As depicted, the process 800 can occur at the CGM simulation system 100, as described throughout this disclosure. The process 800 performs similarly to the process 400 depicted and described in FIG. 4. As depicted, some steps in the process 800 can be performed at different components of the CGM simulation system 100. First, referring to FIG. 8A, in step 802, the input device 102 can obtain data about a first glucose-impacting event (e.g., refer to step 502 in FIG. 5). The processor 106 and/or the conversion module 110 can generate a simulated physiological response can be generated in step 804 (e.g., refer to step 404 in FIG. 4, step 504 in FIG. 5, step 604 in FIG. 6, and step 706 in FIG. 7). Next, the simulated sensor 108 can calculate a simulated glucose value in step 806 (e.g., refer to step 406 in FIG. 4, step 506 in FIG. 5, step 606 in FIG. 6, and step 708 in FIG. 7). The simulated sensor 108 can transmit the simulated glucose value to the real medication delivery system 114 in step 808 (e.g., refer to step 408 in FIG. 4, step 508 in FIG. 5, step 608 in FIG. 6, and step 710 in FIG. 7).

Referring to FIG. 8B, the processor 106 and/or the conversion module 110 can receive data about a second glucose-impacting event from the real medication delivery system 114 in step 810 (e.g., refer to step 410 in FIG. 4, step 510 in FIG. 5, step 610 in FIG. 6, and step 712 in FIG. 7). The processor 106 and/or the conversion module 110 can then generate an expected glucose value in step 812 (e.g., refer to step 412 in FIG. 4, step 512 in FIG. 5, step 612 in FIG. 6, and step 714 in FIG. 7) and determine whether the expected glucose value meets a predetermined threshold level in step 814 (e.g., refer to step 414 in FIG. 4, step 514 in FIG. 5, step 614 in FIG. 6, and step 716 in FIG. 7). If the expected glucose value meets the threshold level, then the process 800 can return to step 802 in FIG. 8A. The steps of the process 800 can then be repeated, as described throughout this disclosure. If, on the other hand, the processor 106 and/or the conversion module 110 determine that the expected glucose value does not meet the threshold level in step 814, then a notification can be generated in step 816 (e.g., refer to step 416 in FIG. 4, step 516 in FIG. 5, step 616 in FIG. 6, and step 718 in FIG. 7) and one or more potential modifications to the medication delivery system 114's configuration can be generated in step 818 (e.g., refer to step 418 in FIG. 4, step 518 in FIG. 5, step 618 in FIG. 6, and step 720 in FIG. 7). In some implementations, the notification in step 816 can be generated by the user device 116 in response to one or more previously discussed steps that are performed at the CGM simulation system 100. In other implementations, the notification can be generated by the CGM simulation system 100 and transmitted to the user device 116 for display.

FIG. 9 is a flowchart of an example process 900 to simulate a communication failure at a medication delivery system. As depicted, the process 900 can occur at the CGM simulation system 100, as described throughout this disclosure. The process 900 performs similarly to the process 400 depicted and described in FIG. 4. The CGM simulation system 100 can be configured to detect faults with a real sensor in the medication delivery system 114. For example, the CGM simulation system 100 can simulate the simulated sensor 108 as being accidentally removed from a patient's body or disconnected from another component of the medication delivery system 114 in step 902. For example, the simulated sensor 108 can generate a signal representative of blood glucose measures that would be detected if an actual sensor (representative by the simulated sensor) were removed from a patient's body or disconnected from another component of the medication delivery system 114. As described throughout this disclosure, the CGM simulation system 100 can transmit a simulated glucose value to the medication delivery system 114 in step 904. The simulation system 100 can receive data about a second glucose-impacting event from the medication delivery system 114 in step 906. Then, the simulation system 100 can generate an expected glucose value in step 908. In step 910, the simulation system 100 can determine whether the expected glucose value meets a predetermined threshold level, as described throughout this disclosure. If it does, then the process 900 can be repeated. Alternatively, the process 900 can end. If it does not, then the CGM simulation system 100 can generate a signal representative of a communication failure in step 912. In step 914, the CGM simulation system 100 transmits the signal to the medication delivery system 114 that will generate and output a notification based on the signal. For example, the medication delivery system 114 can output the notification (e.g., in the form of visual and/or audible message) using a user device (e.g., the user device 116). In step 916, the CGM simulation system 100 receives data representative of the notification that is generated by the medication delivery system 114. In step 918, the CGM simulation system 100 can determine whether the notification was appropriate for the communication failure that was determined earlier by the CGM simulation system 100.

If the notification was appropriate, the process 900 can stop. In some implementations, the process 900 can be repeated. If the notification was not appropriate, the CGM simulation system 100 can determine the medication delivery system 114 does not respond a communication failure between components (e.g., a communication between a sensor and other components such as a pump) in the medication delivery system 114. In addition, the CGM simulation system 100 can accordingly determine an appropriate response and notification to generate based on the simulated disconnection between the simulated sensor 108 and the medication delivery system 114 in step 920. Where the simulated sensor 108 simulates a loss of communication between the simulated sensor 108 and a component of the medication delivery system 114, the notification can include how to address this loss and an appropriate alert for a patient using the medication delivery system 114. For example, the notification can alert the patient that a sensor was removed, accidentally or deliberately, from the patient's body and should be replaced. In other implementations, the notification can alert the patient that the medical infusion device 118 should be restarted to reconnect one or more components of the medication delivery system 114.

FIG. 10 is a flowchart of an example process 1000 to simulate a power loss failure at a medication delivery system. As depicted, the process 1000 can occur at the CGM simulation system 100, as described throughout this disclosure. The process 1000 performs similarly to the process 400 depicted and described in FIG. 4. As depicted, the CGM simulation system 100 can power off the simulated sensor 108 in step 1002. This can simulate a power loss situation that can occur when the medication delivery system 114 is in use by a patient. In this case, the CGM simulation system 100 cannot communicate with the medication delivery system 114 via the simulated sensor 108 because the simulated sensor 108 lost connection with the medical infusion device 118 of the medication delivery system 114. In step 1004, the simulation system 100 can receive data about a glucose-impacting event from the medication delivery system 114. Then, the simulation system 100 can generate an expected glucose value in step 1006. In step 1008, the CGM simulation system 100 can determine whether the expected glucose value meets a predetermined threshold level. The expected glucose value that fails to meet the predetermined threshold level can be considered as a power failure of a sensor in the medication delivery system that is represented by the simulated sensor in the CGM simulation system 100. Although the process 1000 is described primarily for a power failure of a sensor, the process 1000 can be also applicable to power failures of other components, such as a pump, a user device, etc.

If the expected glucose value meets the predetermined threshold value (step 10080), then the process 1000 can be repeated. Alternatively, the process 1000 can end. If it does not (in step 1008), then the simulation system 100 can generate a signal representative of a power failure in step 1010. In step 1012, the CGM simulation system 100 transmits the signal to the medication delivery system 114 that will generate and output a notification based on the signal. For example, the medication delivery system 114 can output the notification (e.g., in the form of visual and/or audible message) using a user device (e.g., the user device 116). By way of example, the notification can indicate that a battery of the medication delivery system 114 needs to be replaced. The medication delivery system 114 can then be reconfigured to provide that notification to patients in real-time, when such failure occurs (step 1014). Thus, in real-time that notification can be displayed on a mobile device (e.g., the user device 116) to a patient at the medication delivery system 114 so that the patient knows about the power failure and how to respond accordingly.

In step 1016, the CGM simulation system 100 receives data representative of the notification that is generated by the medication delivery system 114. In step 1018, the CGM simulation system 100 can determine whether the notification was appropriate for the power failure that was determined earlier by the CGM simulation system 100. If the notification was appropriate, the process 1000 can stop. Alternatively, the process 1000 can be repeated. If the notification was not appropriate, the CGM simulation system 100 can determine the medication delivery system 114 does not respond a power failure of one or more components such as a sensor in the medication delivery system 114. In addition, the CGM simulation system 100 can accordingly determine an appropriate response and notification to generate based on the simulated power failure (step 1020).

Figure 11:
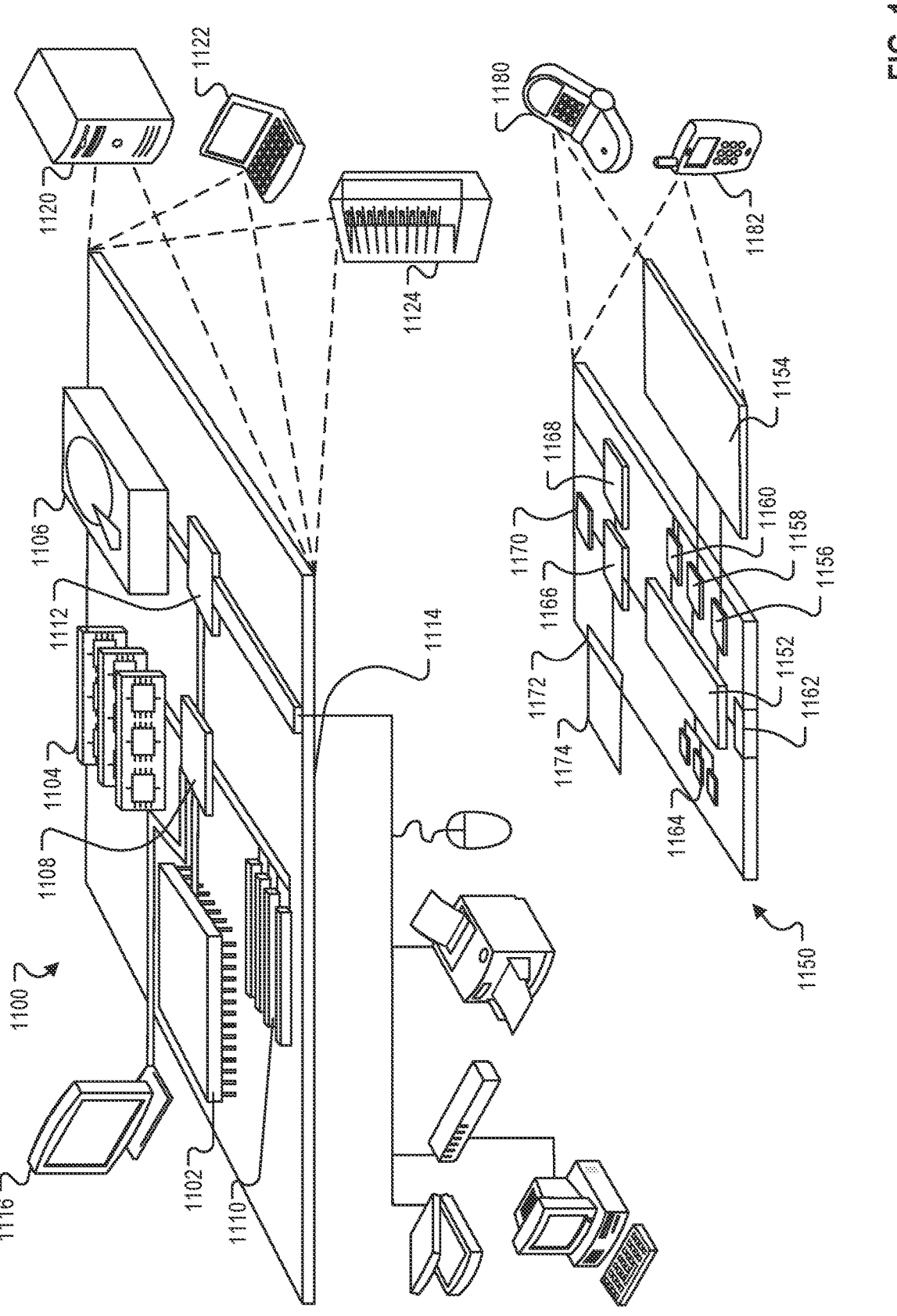
FIG. 11 is a block diagram of computing devices that can be used to implement the systems and methods described in this document.

FIG. 11 is a block diagram of computing devices 1100, 1150 that can be used to implement the systems and methods described in this document, as either a client or as a server or plurality of servers. Computing device 1100 is intended to represent various forms of digital computers, such as laptops, desktops, workstations, personal digital assistants, servers, blade servers, mainframes, and other appropriate computers. Computing device 1150 is intended to represent various forms of mobile devices, such as personal digital assistants, cellular telephones, smartphones, and other similar computing devices. Additionally computing device 1100 or 1150 can include Universal Serial Bus (USB) flash drives. The USB flash drives can store operating systems and other applications. The USB flash drives can include input/output components, such as a wireless transmitter or USB connector that can be inserted into a USB port of another computing device. The components shown here, their connections and relationships, and their functions, are meant to be exemplary only, and are not meant to limit implementations of the inventions described and/or claimed in this document.

Computing device 1100 includes a processor 1102, memory 1104, a storage device 1106, a high speed interface 1108 connecting to memory 1104 and high speed expansion ports 1110, and a low speed interface 1112 connecting to low speed bus 1114 and storage device 1106. Each of the components 1102, 1104, 1106, 1108, 1110 and 1112, are interconnected using various busses, and can be mounted on a common motherboard or in other manners as appropriate. The processor 1102 can process instructions for execution within the computing device 1100, including instructions stored in the memory 1104 or on the storage device 1106 to display graphical information for a GUI on an external input/output device, such as display 1116 coupled to high speed interface 1108. In other implementations, multiple processors and/or multiple buses can be used, as appropriate, along with multiple memories and types of memory. Also, multiple computing devices 1100 can be connected, with each device providing portions of the necessary operations (e.g., as a server bank, a group of blade servers, or a multi-processor system).

The memory 1104 stores information within the computing device 1100. In one implementation, the memory 1104 is a volatile memory unit or units. In another implementation, the memory 1104 is a non-volatile memory unit or units. The memory 1104 can also be another form of computer-readable medium, such as a magnetic or optical disk.

The storage device 1106 is capable of providing mass storage for the computing device 1100. In one implementation, the storage device 1106 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The information carrier is a computer- or machine-readable medium, such as the memory 1104, the storage device 1106, or memory on processor 1102.

The high speed controller 1108 manages bandwidth-intensive operations for the computing device 1100, while the low speed controller 1112 manages lower bandwidth-intensive operations. Such allocation of functions is exemplary only. In one implementation, the high speed controller 1108 is coupled to memory 1104, display 1116 (e.g., through a graphics processor or accelerator), and to high speed expansion ports 1110, which can accept various expansion cards (not shown). In the implementation, low speed controller 1112 is coupled to storage device 1106 and low speed expansion port 1114. The low speed expansion port, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 1100 can be implemented in a number of different forms, as shown in the figure. For example, it can be implemented as a standard server 1120, or multiple times in a group of such servers. It can also be implemented as part of a rack server system 1124. In addition, it can be implemented in a personal computer such as a laptop computer 1122. Alternatively, components from computing device 1100 can be combined with other components in a mobile device (not shown), such as device 1150. Each of such devices can contain one or more of computing device 1100, 1150, and an entire system can be made up of multiple computing devices 1100, 1150 communicating with each other.

Computing device 1150 includes a processor 1152, memory 1164, an input/output device such as a display 1154, a communication interface 1166, and a transceiver 1168, among other components. The device 1150 can also be provided with a storage device, such as a microdrive or other device, to provide additional storage. Each of the components 1150, 1152, 1164, 1154, 1166, and 1168, are interconnected using various buses, and several of the components can be mounted on a common motherboard or in other manners as appropriate.

The processor 1152 can execute instructions within the computing device 1150, including instructions stored in the memory 1164. The processor can be implemented as a chipset of chips that include separate and multiple analog and digital processors. Additionally, the processor can be implemented using any of a number of architectures. For example, the processor 1102 can be a CISC (Complex Instruction Set Computers) processor, a RISC (Reduced Instruction Set Computer) processor, or a MISC (Minimal Instruction Set Computer) processor. The processor can provide, for example, for coordination of the other components of the device 1150, such as control of user interfaces, applications run by device 1150, and wireless communication by device 1150.

Processor 1152 can communicate with a user through control interface 1158 and display interface 1156 coupled to a display 1154. The display 1154 can be, for example, a TFT (Thin-Film-Transistor Liquid Crystal Display) display or an OLED (Organic Light Emitting Diode) display, or other appropriate display technology. The display interface 1156 can comprise appropriate circuitry for driving the display 1154 to present graphical and other information to a user. The control interface 1158 can receive commands from a user and convert them for submission to the processor 1152. In addition, an external interface 1162 can be provide in communication with processor 1152, so as to enable near area communication of device 1150 with other devices. External interface 1162 can provide, for example, for wired communication in some implementations, or for wireless communication in other implementations, and multiple interfaces can also be used.

The memory 1164 stores information within the computing device 1150. The memory 1164 can be implemented as one or more of a computer-readable medium or media, a volatile memory unit or units, or a non-volatile memory unit or units. Expansion memory 1174 can also be provided and connected to device 1150 through expansion interface 1172, which can include, for example, a SIMM (Single In Line Memory Module) card interface. Such expansion memory 1174 can provide extra storage space for device 1150, or can also store applications or other information for device 1150. Specifically, expansion memory 1174 can include instructions to carry out or supplement the processes described above, and can include secure information also. Thus, for example, expansion memory 1174 can be provide as a security module for device 1150, and can be programmed with instructions that permit secure use of device 1150. In addition, secure applications can be provided via the SIMM cards, along with additional information, such as placing identifying information on the SIMM card in a non-hackable manner.

The memory can include, for example, flash memory and/or NVRAM memory, as discussed below. In one implementation, a computer program product is tangibly embodied in an information carrier. The computer program product contains instructions that, when executed, perform one or more methods, such as those described above. The information carrier is a computer- or machine-readable medium, such as the memory 1164, expansion memory 1174, or memory on processor 1152 that can be received, for example, over transceiver 1168 or external interface 1162.

Device 1150 can communicate wirelessly through communication interface 1166, which can include digital signal processing circuitry where necessary. Communication interface 1166 can provide for communications under various modes or protocols, such as GSM voice calls, SMS, EMS, or MMS messaging, CDMA, TDMA, PDC, WCDMA, CDMA2000, or GPRS, among others. Such communication can occur, for example, through radio-frequency transceiver 1168. In addition, short-range communication can occur, such as using a Bluetooth, WiFi, or other such transceiver (not shown). In addition, GPS (Global Positioning System) receiver module 1170 can provide additional navigation- and location-related wireless data to device 1150, which can be used as appropriate by applications running on device 1150.

Device 1150 can also communicate audibly using audio codec 1160, which can receive spoken information from a user and convert it to usable digital information. Audio codec 1160 can likewise generate audible sound for a user, such as through a speaker, e.g., in a handset of device 1150. Such sound can include sound from voice telephone calls, can include recorded sound (e.g., voice messages, music files, etc.) and can also include sound generated by applications operating on device 1150.

The computing device 1150 can be implemented in a number of different forms, as shown in the figure. For example, it can be implemented as a cellular telephone 1180. It can also be implemented as part of a smartphone 1182, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), peer-to-peer networks (having ad-hoc or static members), grid computing infrastructures, and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

The invention claimed is:

1. A method for simulating a glucose monitoring system, wherein the glucose monitoring system includes a medication delivery device configured to dispense medication, the method comprising:
   obtaining, at a simulation system, first data representative of a first glucose-impacting event;
   generating, at the simulation system, second data based on the first data, the second data representative of a simulated physiological response to the first glucose-impacting event;

calculating, at the simulation system, third data based on the second data, the third data representative of a simulated glucose value according to the simulated physiological response;
   transmitting, using the simulation system, the third data to the medication delivery device;
   receiving, at the simulation system, fourth data from the medication delivery device, wherein the medication delivery device generates the fourth data representative of a second glucose-impacting event, and wherein the medication delivery device generates the fourth data based on the third data transmitted from the simulation system;
   generating, at the simulation system, fifth data based on the fourth data, the fifth data representative of an expected glucose value based on the second glucose-impacting event;
   determining, at the simulation system, whether the expected glucose value meets a threshold; and
   generating, at the simulation system, a notification when the expected glucose value does not meet the threshold.

2. The method of claim 1, wherein the simulation system:
   obtains the first data representative of the first glucose-impacting event at a first time, and
   receives the fourth data representative of the second glucose-impacting event at a second time later than the first time.

3. The method of claim 1, wherein obtaining first data representative of a first glucose-impacting event includes:
   receiving, at the simulation system and from a server, the first data representative of the first glucose-impacting event.

4. The method of claim 1, wherein obtaining first data representative of a first glucose-impacting event includes:
   retrieving, at the simulation system, the first data representative of the first glucose-impacting event, wherein the first data is stored in the simulation system.

5. The method of claim 1, wherein the first glucose-impacting event includes at least one of carb ingestion, exogenous insulin delivery, exercise, adjusted physiological parameter, system disconnection, or sensor fault.

6. The method of claim 1, wherein the second glucose-impacting event includes a dosage of the medication being calculated based on the simulated glucose value.

7. The method of claim 1, wherein the glucose monitoring system further comprises:
   a user computing device configured to communicate with the medication delivery device; and
   a server configured to communicate with the user computing device.

8. The method of claim 1, wherein the medication delivery device includes a portable infusion pump.

9. The method of claim 1, wherein the medication delivery device comprises a medication injection pen.

10. The method of claim 1, wherein the simulation system comprises an adaptive learning algorithm configured to generate the second data.

11. The method of claim 1, wherein the notification is generated in real time.

12. A simulation system for simulating a glucose monitoring system, wherein the glucose monitoring system includes a medication delivery device configured to dispense medication, the simulation system comprising:
   an input device configured to obtain first data representative of a first glucose-impacting event;
   a processor in communication with the input device, wherein the processor is configured to generate second data based on the first data, the second data representative of a simulated physiological response to the first glucose-impacting event; and a simulated glucose sensor in communication with the processor, wherein the simulated glucose sensor is configured to:

generate third data based on the second data, the third data representative of a simulated glucose value according to the simulated physiological response; and transmit the third data to the medication delivery device, wherein the processor is further configured to:

receive, from the medication delivery device, fourth data representative of a second glucose-impacting event, wherein the fourth data is generated by the medication delivery device based on the third data transmitted from the simulated glucose sensor.

13. The system of claim 12, wherein the processor is further configured to:

generate fifth data based on the fourth data, the fifth data representative of an expected glucose value based on the second glucose-impacting event;

determine whether the expected glucose value meets a threshold; and generate a notification when the expected glucose value does not meet the threshold.

14. The system of claim 12, wherein the input device is configured to receive a user input of the first data representative of the first glucose-impacting event.

15. The system of claim 12, wherein the input device is configured to receive the first data representative of the first glucose-impacting event from a server.

16. The system of claim 12, further comprising a storage device accessible by the processor, wherein the storage device is configured to store a script and the first data representative of a plurality of glucose-impacting events including the first glucose-impacting event, and wherein the processor is further configured to;

run the script to simulate the plurality of glucose-impacting events over a period of time, and generate the second data based on the plurality of glucose-impacting events.

17. The system of claim 12, wherein the first glucose-impacting event includes at least one of carb ingestion, exogenous insulin delivery, exercise, adjusted physiological parameter, system disconnection, or sensor fault.

18. The system of claim 12, wherein the second glucose-impacting event includes a dosage of the medication being calculated based on the simulated glucose value.

19. The system of claim 12, wherein the first glucose-impacting event relates to a category of patients, wherein the category of patients comprises an age, a type of lifestyle, or a type of diabetes.

20. The system of claim 12, wherein the medication delivery device comprises a medication injection pen.

21. The system of claim 12, wherein the simulation system comprises an adaptive learning algorithm configured to generate the second data.

* * * * *